US009422600B2

(12) United States Patent
Ramu et al.

(10) Patent No.: US 9,422,600 B2
(45) Date of Patent: Aug. 23, 2016

(54) METHODS AND APPARATUSES FOR CHIP-BASED DNA ERROR REDUCTION

(75) Inventors: Senthil Ramu, Boston, MA (US); Joseph Jacobson, Newton, MA (US)

(73) Assignee: Gen9, Inc., Cambridge, MA (US)

( * ) Notice: Subject to any disclaimer, the term of this patent is extended or adjusted under 35 U.S.C. 154(b) by 0 days.

(21) Appl. No.: 13/164,045

(22) Filed: Jun. 20, 2011

(65) Prior Publication Data

US 2012/0028843 A1 Feb. 2, 2012

Related U.S. Application Data

(63) Continuation of application No. PCT/US2010/057405, filed on Nov. 19, 2010.

(60) Provisional application No. 61/264,643, filed on Nov. 25, 2009.

(51) Int. Cl.
| | | |
|---|---|---|
| C12P 19/34 | (2006.01) |
| C12Q 1/68 | (2006.01) |
| C12M 1/34 | (2006.01) |
| C12M 3/00 | (2006.01) |
| C07H 21/02 | (2006.01) |
| C07H 21/04 | (2006.01) |
| C07H 21/00 | (2006.01) |

(52) U.S. Cl.
CPC .................................. *C12Q 1/6848* (2013.01)

(58) Field of Classification Search
USPC .......... 435/6.1, 6.11, 91.1, 183, 283.1, 287.1, 435/287.2, 6.12, 91.2; 436/94, 501; 536/23.1, 24.3, 24.33, 25.3
See application file for complete search history.

(56) References Cited

U.S. PATENT DOCUMENTS

| 4,500,707 | A | | 2/1985 | Caruthers et al. |
|---|---|---|---|---|
| 4,725,677 | A | | 2/1988 | Koster et al. |
| 5,047,524 | A | | 9/1991 | Andrus et al. |
| 5,143,854 | A | | 9/1992 | Pirrung et al. |
| 5,288,514 | A | | 2/1994 | Ellman |
| 5,384,261 | A | | 1/1995 | Winkler et al. |
| 5,510,270 | A | | 4/1996 | Fodor et al. |
| 5,514,789 | A | | 5/1996 | Kempe |
| 5,527,681 | A | | 6/1996 | Holmes |
| 5,541,061 | A | | 7/1996 | Fodor et al. |
| 5,639,603 | A | | 6/1997 | Dower et al. |
| 5,658,802 | A | | 8/1997 | Hayes et al. |
| 5,700,637 | A | | 12/1997 | Southern |
| 5,738,829 | A | | 4/1998 | Kempe |
| 5,770,358 | A | | 6/1998 | Dower et al. |
| 5,830,721 | A | | 11/1998 | Stemmer |
| 5,922,539 | A | * | 7/1999 | Modrich et al. ............. 435/6.11 |
| 5,928,905 | A | | 7/1999 | Stemmer et al. |
| 6,042,211 | A | | 3/2000 | Hudson et al. |
| 6,150,102 | A | | 11/2000 | Mills |
| 6,177,558 | B1 | | 1/2001 | Brennan et al. |
| 6,248,521 | B1 | | 6/2001 | Van Ness et al. |
| 6,297,017 | B1 | * | 10/2001 | Schmidt et al. ............. 435/6.18 |
| 6,375,903 | B1 | | 4/2002 | Cerrina et al. |
| 6,416,164 | B1 | | 7/2002 | Stearns et al. |
| 6,479,652 | B1 | | 11/2002 | Crameri |
| 6,511,849 | B1 | | 1/2003 | Wang |
| 6,514,704 | B2 | | 2/2003 | Bruce |
| 6,521,427 | B1 | | 2/2003 | Evans |
| 6,586,211 | B1 | | 7/2003 | Stahler |
| 6,596,239 | B2 | | 7/2003 | Williams et al. |
| 6,664,388 | B2 | | 12/2003 | Nelson |
| 6,670,127 | B2 | | 12/2003 | Evans |
| 6,800,439 | B1 | | 10/2004 | McGall et al. |
| 6,802,593 | B2 | | 10/2004 | Ellson et al. |
| 6,824,866 | B1 | | 11/2004 | Glazer et al. |
| 6,830,890 | B2 | | 12/2004 | Lockhart et al. |
| 6,833,450 | B1 | | 12/2004 | McGall et al. |
| 6,846,655 | B1 | * | 1/2005 | Wagner et al. ............. 435/91.2 |
| 6,911,132 | B2 | | 6/2005 | Pamula et al. |

(Continued)

FOREIGN PATENT DOCUMENTS

| EP | 1205548 | 5/2002 |
|---|---|---|
| WO | WO90/00626 | 1/1990 |

(Continued)

OTHER PUBLICATIONS

Adessi, C., et al. "Solid phase DNA amplification: characterization of primer attachment and amplification mechanisms," Nucleic Acids Research, 28(20):e87 (8 pages), (2000).

Bar G., et al., "Dendrimer-modified silicon oxide surfaces as platforms for the deposition of gold and silver colloid monolayers: preparation method, characterization, and correlation between microstructure and optical properties," Langmuir, 12(5):1172-1179, (Mar. 6, 1996).

Berthier, E., et al. "Managing evaporation for more robust microscale assays. Part 1: Volume loss in high throughput assays Supplementary Information," Lab Chip, 8:852-859, (Feb. 29, 2008).

Bethell, D., et al. "From monolayers to nanostructured materials: an organic chemist's view of self-assembly," J. Electroanal. Chem., 409:137-143, (1996).

Binkowski, B., et al. "Correcting errors in synthetic DNA through consensus shuffling," Nucleic Acids Research, 33(6):1-8, (2005).

Biswas, I. and Hsieh, P., "Identification and characterization of a thermostable MutS homolog from Thermus aquaticus," J. Biol. Chem, 271(9):5040-5048, (1996).

(Continued)

*Primary Examiner* — Frank Lu
(74) *Attorney, Agent, or Firm* — Greenberg Traurig, LLP; Fang Xie

(57) ABSTRACT

Methods and apparatus relate to reduction of sequence errors generated during synthesis of nucleic acids on a microarray chip. The error reduction can include synthesis of complementary stands (to template strands), using a short universal primer complementary to the template strands and polymerase. Heteroduplex can be formed be melting and re-annealing complementary stands and template strands. The heteroduplexes containing a mismatch can be recognized and cleaved by a mismatch endonuclease. The mismatch-containing cleaved heteroduplexes can be removed from the microarray chip using a global buffer exchange. The error free synthetic nucleic acids generated therefrom can be used for a variety of applications, including synthesis of biofuels and value-added pharmaceutical products.

21 Claims, 7 Drawing Sheets

(56) References Cited

U.S. PATENT DOCUMENTS

| | | | |
|---|---|---|---|
| 6,932,097 | B2 | 8/2005 | Ellson et al. |
| 7,090,333 | B2 | 8/2006 | Mutz et al. |
| 7,183,406 | B2 | 2/2007 | Belshaw |
| 7,262,031 | B2 | 8/2007 | Lathrop |
| 7,303,872 | B2 | 12/2007 | Sussman |
| 7,323,320 | B2 | 1/2008 | Oleinikov |
| 7,498,176 | B2 | 3/2009 | McCormick et al. |
| 7,563,600 | B2 | 7/2009 | Oleinikov |
| 7,820,412 | B2 | 10/2010 | Belshaw |
| 7,879,580 | B2 | 2/2011 | Carr |
| 2001/0024788 | A1* | 9/2001 | Hashimoto ............... 435/6 |
| 2002/0037579 | A1 | 3/2002 | Ellson et al. |
| 2002/0081582 | A1 | 6/2002 | Gao et al. |
| 2003/0047688 | A1 | 3/2003 | Farris et al. |
| 2003/0068633 | A1 | 4/2003 | Belshaw et al. |
| 2003/0108903 | A1* | 6/2003 | Wang et al. ............... 435/6 |
| 2003/0170616 | A1* | 9/2003 | Wang et al. ............... 435/5 |
| 2003/0171325 | A1 | 9/2003 | Gascoyne |
| 2003/0186226 | A1 | 10/2003 | Brennan |
| 2003/0215837 | A1 | 11/2003 | Frey |
| 2004/0086892 | A1* | 5/2004 | Crothers et al. .......... 435/6 |
| 2004/0171047 | A1* | 9/2004 | Dahl et al. ............... 435/6 |
| 2004/0185484 | A1 | 9/2004 | Costa et al. |
| 2004/0234970 | A1* | 11/2004 | Yoo ......................... 435/6 |
| 2006/0008833 | A1 | 1/2006 | Jacobson |
| 2006/0054503 | A1 | 3/2006 | Pamula et al. |
| 2006/0134638 | A1* | 6/2006 | Mulligan et al. .......... 435/6 |
| 2007/0122817 | A1* | 5/2007 | Church et al. ............ 435/6 |
| 2007/0281309 | A1 | 12/2007 | Kong |
| 2008/0009420 | A1* | 1/2008 | Schroth et al. ........... 506/16 |
| 2008/0274513 | A1 | 11/2008 | Shenderov et al. |
| 2010/0304984 | A1* | 12/2010 | Shipman et al. .......... 506/8 |
| 2011/0172127 | A1* | 7/2011 | Jacobson et al. ......... 506/26 |

FOREIGN PATENT DOCUMENTS

| | | |
|---|---|---|
| WO | WO 99/42813 | 8/1999 |
| WO | WO01/88173 | 11/2001 |
| WO | WO 02/24597 | 3/2002 |
| WO | WO 03/040410 | 5/2003 |
| WO | WO 03/046223 | 6/2003 |
| WO | WO 03/054232 | 7/2003 |
| WO | WO 03/064026 | 8/2003 |
| WO | WO 03/064027 | 8/2003 |
| WO | WO 03/064699 | 8/2003 |
| WO | WO 03/065038 | 8/2003 |
| WO | WO 03/066212 | 8/2003 |
| WO | WO 03/100012 | 12/2003 |
| WO | WO 2004/002627 | 1/2004 |
| WO | WO2004/024886 | 3/2004 |
| WO | WO 2004/029586 | 4/2004 |
| WO | WO 2004/031351 | 4/2004 |
| WO | WO 2004/031399 | 4/2004 |
| WO | WO 2004/090170 | 10/2004 |
| WO | WO 2005/059096 | 6/2005 |
| WO | WO2005/071077 | 8/2005 |
| WO | WO 2005/123956 | 12/2005 |
| WO | WO 2006/044956 | 4/2006 |
| WO | WO2006/076679 | 7/2006 |
| WO | WO 2008/024319 | 2/2008 |
| WO | WO 2010/025310 | 3/2010 |
| WO | WO 2011/056872 | 5/2011 |
| WO | WO 2011/066186 | 5/2011 |
| WO | WO2011/066185 | 6/2011 |

OTHER PUBLICATIONS

Blanchard, A., "Synthetic DNA Arrays," Genetic Engineering, 20:111-123, Plenum Press, (1998).

Boal, J., et al., "Cleavage of oligodeoxyribonucleotides from controlled-pore glass supports and their rapid deprotection by gaseous amines," Nucleic Acids Research 24(15):3115-3117, (1996).

Carr, P., et al., "Protein-mediated error correction for de novo DNA synthesis," Nucleic Acids Res., 32(20):e162 (9 pages), (2004).

Cho, S., et al. "Creating, transporting, cutting and merging liquid droplets by electrowetting-based actuation for digital microfluidic circuits," J. of Microelectromechanical Systems, 12(1):70-80, (Feb. 2003).

Cleary, M., et al. "Production of complex nucleic acid libraries using highly parallel in situ oligonucleotide synthesis," Nat Methods., 1(3):241-248, (Dec. 2004).

Colvin, V., et al. "Semiconductor nanocrystals covalently bound to metal surfaces with self-assembled monolayers," J. Am. Chem. Soc., 114(13):5221-5230, 1992.

Duggan, D., et al., "Expression profiling using cDNA microarrays," Nat. Genet., 21:10-14 (Jan. 1999).

Fair, R., "Digital microfluidics: is a true lab-on-a-chip possible?" Microfluid Nonofluid, 3:245-281, (2007).

Fodor, S., et al. "Light-directed, spatially addressable parallel chemical synthesis," Science, 251(4995):767-773, (Feb. 15, 1991).

Golz, S. and Kemper, B., "Enzymatic mutation detection: enrichment of heteroduplexes from hybrid DNA mixtures by cleavage-deficient GST-tagged endonuclease VII," Nucleic Acids Res., 27(15):e7 (4 pages), (Aug. 1, 1999).

Grabar, K., et al., "Preparation and Characterization Monolayers," Anal. Chem., 67:735-743, (1995).

Greenberg, M., et al., "Cleavage of oligonucleotides from solid-phase support using o-nitrobenzyl photochemistry," J. of Org. Chem., 59(4):746-753, (Feb. 1994).

Griffith E. and Aklella, S., "Coordinating Multiple droplets in Planar Array Digital Microfluidics Systems," The International Journal of Robotics Research, 24(11):933-949, (Nov. 2005).

Gulati, S., et al., "Opportunities for microfluidic technologies in synthetic biology," J.R.Soc. Interface, 6: S493-S506, (2009).

Haeberle S. et al. "Microfluidic platforms for lab-on-chip applications," Lab on a Chip, 7(9):1094-1110, (2007).

Hardy, P., et al., "Reagents for the preparation of two oligonucleotides per synthesis (TOPS™)," Nucleic Acids Research, 22(15):2998-3004, (1994).

Holmes, C., et al., "Model studies for new o-nitrobenzyl photolabile linkers: substituent effects on the rates of photochemical cleavage," J. of Org. Chem., 62(8):2370-2380, (Apr. 18, 1997).

Hyman, E., "A new method of sequencing DNA," Analytical Biochemistry, 174(2):423-436, (Nov. 1, 1988).

Kahl, J., et al., "High-Yielding Method for On-Column Derivatization of Protected Oligodeoxy- nucleotides and Its Application to the Convergent Synthesis of 5',3'-Bisconjugates," J. of Org. Chem., 63(15):4870-4871, (Jul. 8, 1998).

Kahl, J., and Greenberg, M., "Solution-Phase Bioconjugate Synthesis Using Protected Oligonucleotides Containing 3'-Alkyl Carboxylic Acids," J. of Org. Chem., 64(2):507-510, (1999).

Kelly, B., et al., "Miniaturizing chemistry and biology in microdroplets," Chem. Commun., 1773-1788, (2007).

Kong, D., et al., "Parallel gene synthesis in a microfluidic device," Nucleic Acids Research, 35(8):1-9, (2007).

Leamon, J., et al., "A massively parallel PicoTiterPlate™ based platform for discrete picoliter-scale polymerase chain reactions," Electrophoresis, 24(21):3769-3777, (Nov. 2003).

Liu, Y., et al., "DNA ligation of ultramicrovolume using EWOD microfluidic system with coplanar electrodes: DNA ligation of ultramicrovolume using a EWOD microfluidic system," J. of Micromechanics and Microengineering, 18(4):45017 (7 pages), (2008).

Margulies, M., et al., "Genome sequencing in microfabricated high-density picolitre reactors," Nature, 437(7057):376-380, (Sep. 15, 2005).

McGall, G., et al., "Light-directed synthesis of high-density oligonucleotide arrays using semiconductor photoresists," PNAS, 93(24):13555-13560, (Nov. 26, 1996).

Metzker, M., et al., "Termination of DNA synthesis by novel 3'-modifieddeoxyribonucleoside 5'-triphosphates," Nucieic Acids Research, 22(20):4259-4267, (1994).

Mitra, R., et al., "Fluorescent in situ sequencing on polymerase colonies," Analytical Biochemistry, 320:55-65, (2003).

Oleykowski, C., et al., "Mutation detection using a novel plant endonuclease," Nucleic Acids Res., 26(20):4597-4602, (Oct. 15, 1998).

(56) References Cited

OTHER PUBLICATIONS

Pon., R., "Solid-phase supports for oligonucleotide synthesis," Methods Mol. Biol. 20:465-496, (1993).

Richmond, K., et al., "Amplification and assembly of chip-eluted DNA (AACED): a method for high-throughput gene synthesis," Nucleic Acids Res., 32(17):5011-5018, (2004).

Schaerli, Y., et al., "Continuous-Flow polymerase Chain reaction of single-copy DNA Micorfluidic Microdroplets," Anal. Chem., 81:302-306, (2009).

Seo, T., et al., "Four-color DNA sequencing by synthesis on a chip using photocleavable fluorescent nucleotides," PNAS, 102(17):5926-5933, (Apr. 26, 2005).

Shabarova, Z., et al. "Chemical ligation of DNA: the first non-enzymatic assembly of a biologically active gene," Nucl. Acids Res., 19(15):4247-4251, (1991).

Shendure, J., et al., "Accurate Multiplex Polony Sequencing of an Evolved Bacterial Genome," Science, 309:1728-1732, (Sep. 9, 2005).

Stekel, D., "Microarrays: Making Them and Using Them in Microarray Bioinformatics," Cambridge University Press, (10 pages), 2003.

Tian, J., et al., "Accurate multiplex gene synthesis from programmable DNA microchips," Nature, 432:1050-1054, (Dec. 2004).

Verma, S. and Eckstein, F., et al., "Modified oligonucleotides: Synthesis and Strategy for Users," Annu. Rev. Biochem., 67:99-134, (1998).

Xu, Y. and Kool, E., et al., "A Novel 5'-Iodonucleoside allows efficient nonenzymatic ligation of single-stranded and duplex DNAs," Tetrahedron Lett., 38(32): 5595-5598, (Aug. 11, 1997).

Xu, Y. and Kool, E., et al., "High sequence fidelity in a non-enzymatic DNA autoligation reaction," Nuc. Acids Res., 27(3): 875-881, (1999).

Xu, Y., et al., "Nonenzymatic autoligation in direct three-color detection of RNA and DNA point mutations," Nat. Biotech., 19:148-152, (Feb. 2001).

Zhou X. et al. "Microfluidic PicoArray synthesis of oligodeoxynucleotides and simultaneous assembling of multiple DNA sequences" Nucleic Acids Research, 2004, vol. 32, No. 18, pp. 5409-5417.

Zielke, P. and Szymczyk, J., "Experimental investigation of the motion and deformation of droplets on surfaces with a linear wettability gradient," Eur. Phys. J. Special Topics, 166:155-158, (Jan. 2009).

International Search report for International Patent Application No. PCT/US2010/057405 mailed Mar. 31, 2011.

Beer, N., et al., "On-chip, real time single-copy polymerase chain reaction in picoliter droplets," Analytical Chemistry, 79(22):8471-8475, (Nov. 15, 2007).

Fidalgo, L., et al., "Surface induced droplet fusion in microfluidic devices," Lab on Chip, 7(8)984-986, (2007).

Teh, S-Y, et al., "Droplet microfluidics," Lab on Chip, 8(2), (2008).

Zhang, C., et al., "PCR microfluidic devices for DNA amplification," Biotechnology Advances, 24(3):243-284, 2006.

Stemmer, et al., "Single-step assembly of a gene and entire plasmid from large numbers of oligodeoxyribonucleotides", Gene, vol. 164, pp. 49-53, (1995).

Stemmer, Willem P.C., "DNA shuffling by random fragmentation and reassembly: In vitro recombination for molecular evolution", Proc. Natl. Acad. Sc. USA, vol. 91, pp. 10747-10751, Oct. 1994.

\* cited by examiner

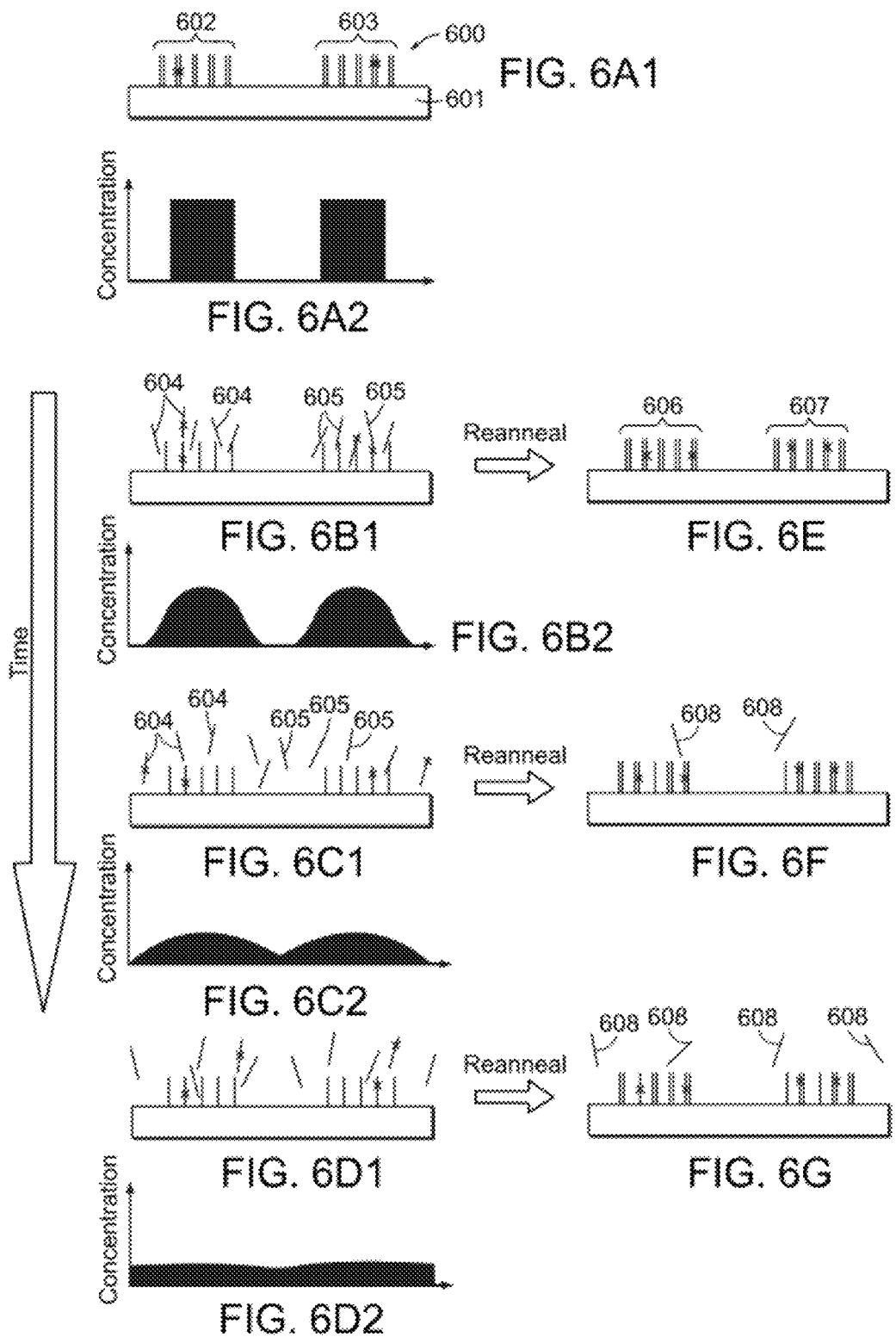

METHODS AND APPARATUSES FOR CHIP-BASED DNA ERROR REDUCTION

RELATED APPLICATIONS

This application is a continuation of International Application No. PCT/US2010/057405, filed Nov. 19, 2010, now International Publication No. WO2010/025310, which claims the benefit of U.S. provisional patent application Ser. No. 61/264,643, filed Nov. 25, 2009, the entire contents of both of which applications are hereby incorporated by reference in their entirety.

FIELD OF THE INVENTION

Methods and apparatuses provided herein relate to the synthesis and assembly of high fidelity nucleic acids and nucleic acid libraries having a predefined sequence using microvolume reactions. More particularly, methods and apparatuses are provided for polynucleotide synthesis, error reduction, hierarchical assembly, and/or sequence verification on a solid support. In some embodiments, pico-liter and sub pico-liter dispensing and droplet moving technologies are applied to access and manipulate the oligonucleotides on DNA microarrays.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive biomolecular priming reactions efficiently. Current methods for assembling small numbers of variant nucleic acids cannot be scaled up in a cost-effective manner to generate large numbers of specified variants. As such, a need remains for improved methods and devices for high-fidelity gene assembly and the like.

Furthermore, oligonucleotides on microchips are generally synthesized via chemical reactions. Spurious chemical reactions cause random base errors in oligonucleotides. One of the critical limitations in chemical nucleic acid synthesis is the error-rate. The error rate of chemically-synthesized oligonucleotides (deletions at a rate of 1 in 100 bases and mismatches and insertions at about 1 in 400 bases) exceeds the error rate obtainable through enzymatic means of replicating an existing nucleic acid (e.g., PCR). Therefore, there is an urgent need for new technology to produce high-fidelity polynucleotides.

SUMMARY

Aspects of the invention relate to methods and apparatuses for preparing and/or assembling high fidelity polymers. Also provided herein are devices and methods for processing nucleic acid assembly reactions and assembling nucleic acids. It is an object of this invention to provide practical, economical methods of synthesizing custom polynucleotides. It is a further object to provide a method of producing synthetic polynucleotides that have lower error rates than synthetic polynucleotides made by methods known in the art.

According to one embodiment, the invention provides a method for producing high fidelity oligonucleotides on a solid support, comprising the steps of exposing a plurality of support-bound single-stranded oligonucleotides comprising a predefined sequence to a polymerase enzyme under conditions suitable for a template-dependent synthesis reaction, thereby to produce a plurality of double-stranded oligonucleotides, each of which comprises a support-bound oligonucleotide and a synthesized complementary oligonucleotide; denaturing the plurality of double-stranded oligonucleotides such that the synthesized oligonucleotides are released from the support-bound oligonucleotides into a solution; reannealing the synthesized oligonucleotides to the support-bound oligonucleotides, thereby to produce reannealed double-stranded oligonucleotides; and exposing the reannealed double-stranded oligonucleotides to a mismatch recognizing and cleaving component under conditions suitable for cleavage of reannealed double-stranded oligonucleotides containing a mismatch.

In one aspect, the invention relates to a method for producing high fidelity oligonucleotides on a solid support. The method includes synthesizing a first plurality of oligonucleotides in a chain extension reaction using a second plurality of oligonucleotides as templates. The second plurality of oligonucleotides are immobilized on a solid support and comprises an error-containing oligonucleotide having a sequence error at an error-containing position. The chain extension reaction produces a first plurality of duplexes. The method also includes melting the first plurality of duplexes to release the first plurality of oligonucleotides from the second plurality of oligonucleotides, wherein the first plurality of oligonucleotides comprise error-free oligonucleotides that are free of error at the error-containing position of the error-containing oligonucleotide. The method further includes contacting the first plurality of oligonucleotides with the second plurality of oligonucleotides under hybridization conditions to form a second plurality of duplexes. The second plurality of duplexes comprises a mismatch-containing heteroduplex formed between the error-containing oligonucleotide and one of the error-free oligonucleotides. The method also includes removing at least a portion of the mismatch-containing heteroduplex by a mismatch recognizing and cleaving component, thereby producing high fidelity oligonucleotides. In some embodiments, the method further includes after the removing step, selectively melting away truncations.

In another aspect, the invention relates to a method of assembling nucleic acid polymers. The method includes producing two or more pools of high fidelity oligonucleotides according to the methods described herein. The method also include melting desirable pools of high fidelity oligonucleotides into a solution, combining the desirable pools of high fidelity oligonucleotides into a reaction volume, and subjecting the reaction volume to conditions suitable for one or more of hybridization, ligation, and/or chain extension.

In various embodiments, the second plurality of oligonucleotides are chemically synthesized on the solid support and immobilized within one or more features on the solid support. The second plurality of oligonucleotides can include oligonucleotides having substantially the same sequence. The second plurality of oligonucleotides can be deposited at one feature on the solid support, or at two or more features on the solid support. The second plurality of oligonucleotides can be of two or more different sequences and each sequence is found at a different feature on the solid support. In some embodiments, the solid support is a microarray.

In some embodiments, the first plurality of oligonucleotides is enzymatically synthesized on the solid support. One or more of the first plurality of oligonucleotides can diffuse in a fluid when melted off and not duplexed with the second plurality of oligonucleotides.

Some aspects of the invention relate to a method of producing at least one oligonucleotide having a predefined sequence on a solid support, the method comprising (a) synthesizing on a solid support a first plurality of double-stranded oligonucleotides using a second plurality of oligonucleotides as templates; (b) releasing the first plurality of oligonucleotides from the second plurality of oligonucleotides within an isolated microvolume; (c) contacting the second plurality of oligonucleotides with the first plurality of oligonucleotides under hybridization conditions to form a second plurality of double-stranded oligonucleotides within the isolated volume; (d) contacting and cleaving the second plurality of double-stranded oligonucleotides with a mismatch binding agent, wherein the mismatch binding agent selectively binds and cleaves the double-stranded oligonucleotides comprising a mismatch; and (e) removing the double-stranded oligonucleotides comprising the mismatch thereby producing error-free oligonucleotides. In some embodiments, the first plurality of oligonucleotides is released under denaturing conditions. In some embodiments, the method further comprises releasing error-free oligonucleotides in solution.

In some embodiments, the second plurality of oligonucleotides is bound to a discrete feature of the solid support and the feature is selectively hydrated thereby providing the second plurality of oligonucleotide within the isolated volume. The feature can be selectively hydrated by spotting a solution comprising a polymerase, dNTPs, a solution promoting primer extension, at least one primer wherein the primer is complementary to a primer binding site on the second plurality of oligonucleotides.

In certain embodiments, the mismatch recognizing and cleaving component comprises a mismatch endonuclease. In one embodiment, the mismatch endonuclease is CEL1. In some embodiments, the mismatch recognizing and cleaving component performs chemical cleavage. After cleaving, certain embodiments can also include removing the cleaved heteroduplex having the mismatch by buffer exchange.

Other features and advantages of the devices and methods provided herein will be apparent from the following detailed description, and from the claims. The claims provided below are hereby incorporated into this section by reference. The various embodiments described herein can be complimentary and can be combined or used together in a manner understood by the skilled person in view of the teachings contained herein.

BRIEF DESCRIPTION OF THE FIGURES

FIG. 5 shows exemplary methods to produce deposited micro-volumes suitable for shuffling. FIG. 5C1 shows a substrate fully immersed in a fluid (511). FIG. 5C2 shows the resulting micro-volumes.

FIG. 6 illustrates exemplary methods using local diffusion to achieve shuffling without micro-volumes. FIG. 6A1 shows the setting prior to melting with surface-attached homoduplexes. FIG. 6A2 shows the concentration of duplexes at two adjacent positions on the substrate. FIG. 6B1 shows the melting at a time immediately after the temperature increases. FIG. 6B2 shows the concentration of duplexes at two adjacent positions on the substrate. FIG. 6E shows the result after reannealing of the molecules according to one embodiment. FIG. 6C1 shows the melting at a later time than that of FIG. 6B1. FIG. 6C2 shows the concentration of duplexes at two adjacent positions on the substrate. FIG. 6F shows the result after reannealing of the molecules according to one embodiment. FIG. 6D1 shows the melting at a later time than that of FIG. 6C1. FIG. 6D2 shows the concentration of duplexes at two adjacent positions on the substrate. FIG. 6G shows the result after reannealing of the molecules according to one embodiment.

FIG. 7 shows exemplary methods using evaporating fast shuffling.

DETAILED DESCRIPTION OF THE INVENTION

Figure 1:
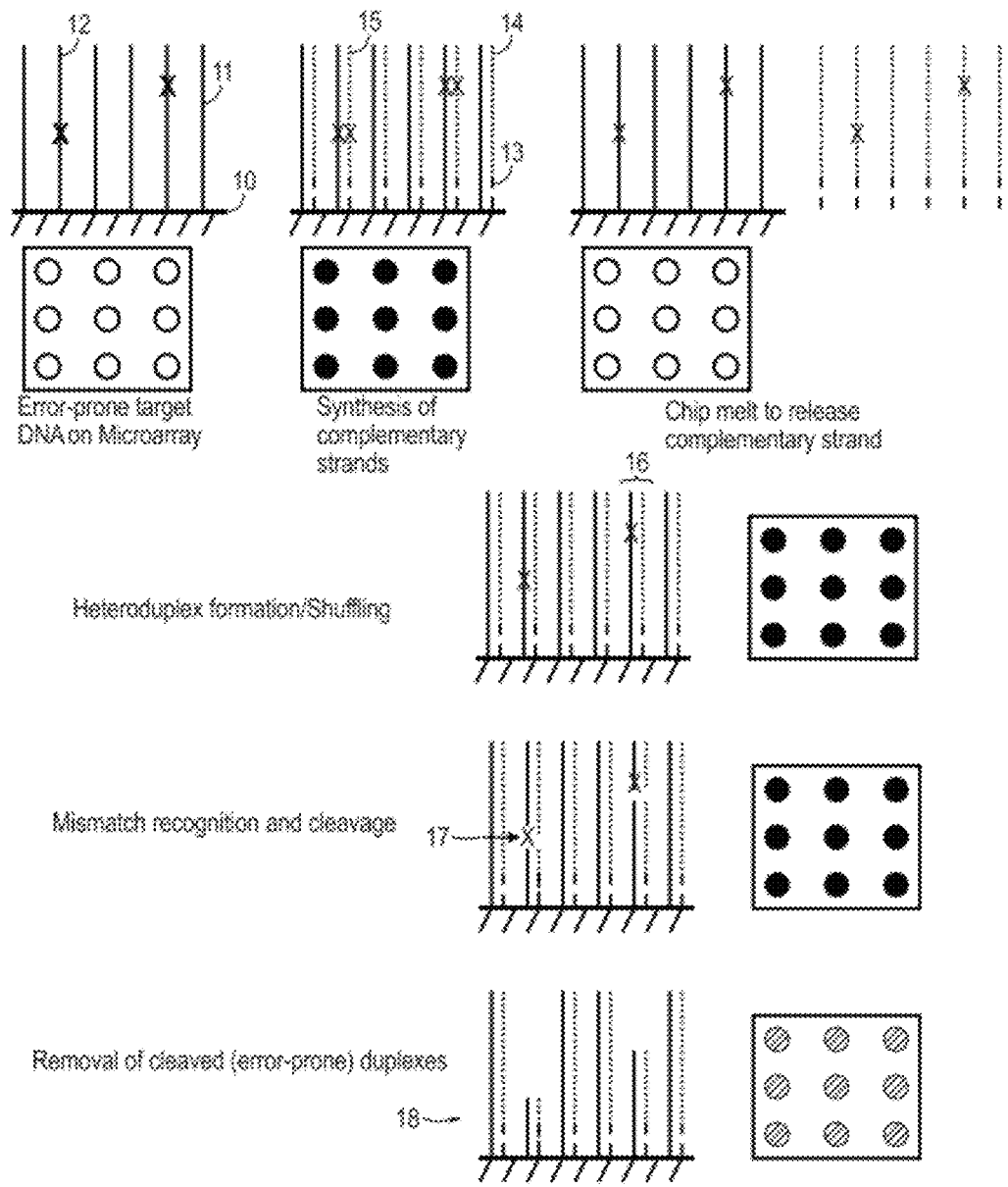
FIG. 1 illustrates an exemplary method of producing high fidelity oligonucleotides on a DNA microarray where heteroduplex formation is followed by mismatch cleavage.

Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predetermined sequence" or "predefined" means that the sequence of the polymer is known and chosen before synthesis or assembly of the polymer. In particular, aspects of the invention are described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequences being determined based on the sequence of the final polynucleotides constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein.

In some embodiments, the assembly procedure may include several parallel and/or sequential reaction steps in which a plurality of different nucleic acids or oligonucleotides are synthesized or immobilized, amplified, and are combined in order to be assembled (e.g., by extension or ligation as described herein) to generate a longer nucleic acid product to be used for further assembly, cloning, or other applications (see U.S. provisional application 61/235,677 and PCT application PCT/US09/55267, now International Publication No. WO2010/025310, which are incorporate herein by reference in their entirety). Amplification and assembly strategies provided herein can be used to generate very large libraries representative of many different nucleic acid sequences of interest.

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences.

Accordingly, one aspect of the technology provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, about 91%, about 92%, about 93%, about 94%, about 95%, about 96%, about 97%, about 98%, about 99%, or more of the sequences are predetermined sequences of interest).

Oligonucleotides can be used as building blocks for DNA synthesis and can be synthesized in single strands on a solid support (e.g. microarray chip surface) using inkjet and other technologies. In nucleic acid assembly process, synthetic oligonucleotides can be used to assemble or amplify DNA into large size DNA constructs. During enzymatic amplification, the error in sequence is faithfully replicated. As a result, DNA population synthesized by this method contains both error-free and error-prone sequences. In some embodiments, since synthetic oligonucleotides can contain incorrect sequences due to errors introduced during oligonucleotide synthesis, it can be useful to remove nucleic acid fragments that have incorporated one or more error-containing oligonucleotides during assembly. In some embodiments, one or more assembled nucleic acid fragments may be sequenced to determine whether they contain the predetermined sequence or not. This procedure allows fragments with the correct sequence to be identified. In other embodiments, other techniques may be used to remove error containing nucleic acid fragments. Such nucleic acid fragments can be nascently synthesized oligonucleotides or assembled nucleic acid polymers. It should be appreciated that error containing-nucleic acids can be double-stranded homoduplexes having the error on both strands (i.e., incorrect complementary nucleotide(s), deletion(s), or addition(s) on both strands), because the assembly procedure may involve one or more rounds of polymerase extension (e.g., during assembly or after assembly to amplify the assembled product) during which an input nucleic acid containing an error may serve as a template thereby producing a complementary strand with the complementary error. In certain embodiments, a preparation of double-stranded nucleic acid fragments may be suspected to contain a mixture of nucleic acids that have the correct sequence and nucleic acids that incorporated one or more sequence errors during assembly. In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands can reanneal with a complementary strand that does not contain any error or that contains one or more different errors (e.g. errors at different positions). As a result, error-containing strands can end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of nucleic acid fragments, the amount or frequency of error containing nucleic acids can be reduced.

Heteroduplex formation thus takes place through a process that can be understood as shuffling, by which nucleic acid strands from different populations can be hybridized with one another so that perfect match and mismatch-containing duplexes can be formed. Suitable method for removing heteroduplex molecules include chromatography, electrophoresis, selective binding of heteroduplex molecules, etc. One requirement for the selective binding agent for use in this process is that it binds preferentially to double stranded DNA having a sequence mismatch between the two strands. In some embodiments, such agent can be a mismatch endonuclease. The term "endonuclease" in general refers to an enzyme that can cleave DNA internally. The term "mismatch" or "base pair mismatch" indicates a base pair combination that generally does not form in nucleic acids according to Watson and Crick base pairing rules. For example, when dealing with the bases commonly found in DNA, namely adenine, guanine, cytosine and thymidine, base pair mismatches are those base combinations other than the A-T and G-C pairs normally found in DNA. As described herein, a mismatch may be indicated, for example as C/C meaning that a cytosine residue is found opposite another cytosine, as opposed to the proper pairing partner, guanine. As used herein "heteroduplex" oligonucleotide refers to a double-stranded oligonucleotide formed by annealing single strands oligonucleotides where the strands, when annealed have unpaired regions such as base-pair mismatch, insertion/deletion loop(s) and or nucleotide(s) gap(s). In one aspect, the invention relates to a method for producing high fidelity oligonucleotides on a solid support. The method includes synthesizing a first plurality of oligonucleotides in a chain extension reaction using a second plurality of oligonucleotides as templates. The second plurality of oligonucleotides are immobilized on a solid support and likely comprises both error-free and error-containing oligonucleotides having a sequence error at an error-containing position. The chain extension reaction produces a first plurality of double-stranded oligonucleotides or duplexes (homoduplexes and/or heteroduplexes). The method also includes melting off or denaturing the first plurality of duplexes to release the first plurality of oligonucleotides from the second plurality of oligonucleotides, wherein the first plurality of oligonucleotides comprise error-free oligonucleotides that are free of error at the error-containing position of the error-containing oligonucleotide. The method further includes contacting the first plurality of oligonucleotides with the second plurality of oligonucleotides under hybridization or annealing conditions to form a second plurality of duplexes. The second plurality of duplexes comprise a mismatch-containing heteroduplex formed between the error-containing oligonucleotide and one of the error-free oligonucleotides. The method also includes removing at least a portion of the mismatch-containing heteroduplex by a mismatch recognizing and cleaving component, thereby producing high fidelity oligonucleotides. In some embodiments, the method further includes after the removing step, selectively melting away truncations.

FIG. 1 shows an exemplary method for producing high fidelity oligonucleotides on a DNA microarray where heteroduplex formation is followed by mismatch cleavage. The microarray contains chemically synthesized oligonucleotides that are immobilized on chip surface 10. The chemically synthesized oligonucleotides, as discussed above, likely contain both error-free template strand 11 and error-prone template strand 12. By way of example, in a chain extension reaction (e.g., PCR) using primer 13 (e.g., a universal amplification primer), the chemically synthesized oligonucleotides can serve as template strands for producing complementary strands. The resulting products can include error-free complementary strand 14 (complementary to error-free template strand 11) and error-prone amplified complementary strand 15 (complementary to error-prone template strand 12). Under melting conditions (e.g., an increased temperature at solid support or chip surface 10), the complementary strands are separated from the template strands. After shuffling, heteroduplex 16 can be formed between an error-prone template strand and an error-free complementary strand. Heteroduplex 16 can then be recognized and cleaved by a component 17 (e.g., Surveyor™ endonuclease). Subsequent removal of cleaved, error-prone duplexes can result in an error-free chip surface 18.

Heteroduplex recognition and cleavage can be achieved by applying a mismatch binding agent to the reaction mix. In some embodiments, the mismatch binding agent is a mismatch specific endonuclease. In some embodiment, a mismatch-binding protein tethered or fused to a nuclease can be used.

One preferred mismatch endonuclease is a CEL1 endonuclease which has a high specificity for insertions, deletions and base substitution mismatches and can detect two polymorphisms which are five nucleotides apart form each other. CEL1 is a plant-specific extracellular glycoprotein that can cleave heteroduplex DNA at all possible single nucleotide mismatches, 3' to the mismatches (Oleykowski C A et al, 1998, Nucleic Acids Res. 26: 4596-4602). CEL1 is useful in mismatch detection assays that rely on nicking and cleaving duplex DNA at insertion/deletion and base substitution mismatches. In an exemplary embodiment, a Surveyor™ Nuclease (Transgenomic Inc.) may be added to a reaction volume containing the oligonucleotide duplexes. Surveyor™ Nuclease is a mismatch specific endonuclease that cleaves all types of mismatches such as single nucleotide polymorphisms, small insertions or deletions. Addition of the endonuclease results in the cleavage of the double-stranded oligonucleotides at the site or region of the mismatch. The remaining portion of the oligonucleotide duplexes can then be melted at a lower and less stringent temperature (e.g. stringent melt) needed to distinguish a single base mismatch. In some embodiments, the error-free oligonucleotides are released in solution.

The mismatch-containing duplexes from the population can be preferably cleaved by mismatch specific CEL1 endonuclease. In some embodiments, other mismatch binding proteins that selectively (e.g., specifically) bind to heteroduplex nucleic acid molecules may be used. One example includes using MutS, a MutS homolog, or a combination thereof to bind to heteroduplex molecules. MutS from *Thermus aquaticus* can be purchase commercially from the Epicenter Corporation, Madison, Wis., Catalog No. SP72100 and SP72250. The gene sequence for the protein is also known and published in Biswas and Hsieh, Jour. Biol. Chem. 271:5040-5048 (1996) and is available in GenBank, accession number U33117. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutSα) recognizes base mismatches and single nucleotide insertion/deletion loops, while the MSH2-MSH3 complex (also known as MutSβ) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*); Taq MutS (from *Thermus aquaticus*); Apy MutS (from *Aquifex pyrophilus*); Tma MutS (from *Thermotoga maritima*); any other suitable MutS; or any combination of two or more thereof.

In some embodiments, small molecules capable to bind to specific nucleotide mismatches can be designed and synthesized. For example, dimeric napthyridine 1, a synthetic ligand that binds to a G-G mismatch. A cocktail of such ligands which, in combination, recognizes all possible mismatches could replace CEL1. Other protein agents that can differentiate between matched and unmatched duplexes could also be used. For example, the T7 endonuclease I will specifically cleave a DNA strand at a mismatch, and it would be possible to use this enzyme as a catalytic destroyer of mismatched sequences or to inactivate the cleavage function of this enzyme for use in this process as a mismatch binding agent. T4 endonuclease VII will specifically bind and cleave DNA at duplex mismatches and a mutant version of this enzyme has already been engineered that lacks the nuclease activity but retains the ability to bind mutant duplex DNA molecules (Golz and Kemper, Nucleic Acids Research, 27:e7 (1999)). SP nuclease is a highly active nuclease from spinach that incises all mismatches except those containing a guanine residue, and this enzyme could also be engineered to remove the cleavage activity or used directly. Two or more of these binding agents could be combined to either provide further stringency to the filtration or to cover all types of sequence errors if one agent does not bind to all possible mismatches.

Some embodiments of the device and methods provided herein use oligonucleotides that are immobilized on a surface or substrate. As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature is chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

Arrays may be constructed, custom ordered or purchased from a commercial vendor (e.g., Agilent, Affymetrix, Nimblegen). Oligonucleotides are attached, spotted, immobilized, surface-bound, supported or synthesized on the discrete features of the surface or array as described above. Oligonucleotides may be covalently attached to the surface or deposited on the surface. Various methods of construction are well known in the art e.g. maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510, 270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles. Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g. ink jet). In some embodiments, oligonucleotides are spotted on a support using, for example, a mechanical wave actuated dispenser.

Methods and devices provided herein involve amplification and/or small assembly reaction volumes such as microvolumes, nanovolumes, picovolumes or sub-picovolumes. Accordingly, aspects of the invention relate to methods and devices for amplification and/or assembly of polynucleotides in small volume droplets on separate and addressable features of a support. For example, a plurality of oligonucleotides complementary to surface-bound single stranded oligonucleotides is synthesized in a predefined reaction microvolume of solution by template-dependant synthesis. In some embodiments, predefined reaction microvolumes of between about 0.5 pL and about 100 nL may be used. However, smaller or larger volumes may be used. In some embodiments, a mechanical wave actuated dispenser may be used for transferring volumes of less than 100 nL, less than 10 nL, less than 5 nL, less than 100 pL, less than 10 pL, or about 0.5 pL or less. In some embodiments, the mechanical wave actuated dispenser can be a piezoelectric inkjet device or an acoustic liquid handler. In a preferred embodiment, a piezoelectric inkjet device is used and can deliver picoliter solutions in a very precise manner on a support as described herein.

Aspects of the invention relate to the manipulation of sub-microvolumes on a substrate and to the control of the movement of micro-volumes on a substrate. It is a well-known phenomenon that the surfaces of most normally solid substrates, when contacted with a solution, have a characteristic degree of non-wettability. That is, aqueous solutions do not spread on the solid surface but contract to form droplets. Accordingly, preferable supports have surface properties, primarily surface tension and wettability properties that allow droplet formation when small volumes are dispensed onto the addressable feature. In some embodiments, the microvolume is bounded completely or almost completely by free surface forming a droplet or microdrop. One skilled in the art will understand that the shape of the droplet will be governed and maintained by the contact angle of the liquid/solid interaction, surface tension of the liquid as well as by surface energy. Adhesive forces between a liquid and solid will cause a liquid drop to spread across the surface whereas cohesive forces within the liquid will cause the drop to ball up and avoid contact with the surface. For liquid, the surface energy density is identical to the surface tension. Surface tension is that property of matter, due to molecular forces, which exists in the surface film of all liquids and tends to bring the contained volume into a form having the least possible superficial area. In some embodiments, the surface is partitioned into discrete regions where the surface contact angles of the discrete region differ for the fluid of interest. As used herein the term "contact angle" refers to a quantitative measure of the wetting of a solid by a liquid. A contact angle is defined as the angle formed by a liquid at the three phase boundary where vapor (gas, e.g., atmosphere), liquid and solid intersect. For example, in the case of a micro-volume droplet dispensed on a horizontal flat surface, the shape of the micro-volume droplet will be determined by the Young equilibrium equation:

$$0 = \gamma_{SV} - \gamma_{SL} - \gamma \cos \theta_C$$

wherein $\gamma_{SV}$ is the solid-vapor interfacial energy; $\gamma_{SL}$ is the solid-liquid interfacial energy and $\gamma$ is the liquid-vapor energy (i.e. surface tension) and $\Theta_C$ is the equilibrium contact angle.

It will be understood that for contact angle values $\Theta_C$ less than 90°, the liquid will spread onto the solid surface. For example, very hydrophilic surfaces have a contact angle of 0° to about 30°. In the case of aqueous solutions and highly hydrophilic support, the contact angle $\Theta_C$ will be close to 0°, and the aqueous solution or droplet will completely spread out on the solid surface (i.e., complete wetting of the surface). If complete wetting does not occur, the liquid will from a droplet. On the contrary, for contact angle values $\Theta_C$ equal to or greater than 90°, the liquid will rest on the surface and form a droplet on the solid surface. The shape of the droplet is determined by the value of the contact angle. In the case of aqueous solutions and highly hydrophobic surfaces, liquid will bead up. In some embodiments, the support is chosen to have a surface energy and surface contact angle that do not allow the droplets to spread beyond the perimeter of the feature. Furthermore, on an ideal surface the droplets will return to their original shapes if they are disturbed, for example after addition of a miscible or non-miscible solution. In some embodiments, the surface is partitioned into regions where the surface contact angles of the regions differ for the liquid of interest. In some embodiments, theses regions correspond to the discrete features of the substrate. In a preferred embodiment, the surface is partitioned into regions by modifiers. Modifiers may be added to specific locations of the substrate's surface. In some cases, the surface will be partitioned into regions comprising modifiers and non-modifier surface areas. In some embodiments, the non-modifier regions correspond to the unmodified substrate. Yet, in other embodiments, the non-modifiers regions correspond to a surface of any arbitrary modification or any modifier that is different than the modifier at a region that corresponds to a feature of a support. In some embodiments, the modifiers are oligomers. For example, the modifiers correspond to nucleic acids and are modifying a set of discrete features of the substrate. Modifiers can have circular, square, trapezoid, or any geometrical shape or any combination thereof. In some embodiments, modifiers are arranged in a grid-like pattern or in any other different configurations. The pattern is not restricted to any design. For example, the modifiers may be arranged in a randomly formed pattern. Patterning may be formed by any process known in the art. For example, arranged patterning or random patterning may be formed by processes such as block co-polymer surface self assembly. In other embodiments, the substrate surface is partitioned into regions by at least two different modifiers regions as discussed herein. In some embodiments, the surface contact angle of the modifiers ($\Theta_M$) is different than the surface contact angle of the non-modifier region ($\Theta_{NM}$). For example, the surface contact angle of the modifiers may be greater than the surface contact angle of the surface or the non-modifier regions ($\Theta_M > \Theta_{NM}$). Alternatively, the surface contact angle of the non-modifier regions is greater than the surface contact angle of the modifiers ($\Theta_M < \Theta_{NM}$). In the context of aqueous solutions, the modifiers surfaces may be more hydrophilic than the surface of the non-modifiers regions (i.e. surface contact angle of the modifiers is smaller than the surface contact angle of the surface or non-modifier regions). Alternatively, the modifiers surfaces may be more hydrophobic than the surface of the non-modifiers surface regions (i.e., surface contact angle of the modifiers is smaller than the surface contact angle of the surface or non-modifier regions). In an exemplary embodiment, modifiers are oligonucleotides and the surface of the modifier regions is more hydrophilic than the surface of the non-modifier regions. In other embodiments, the totality or a substantial part of the support or surface is covered with at least two different modifiers. The at least two different modifiers may be patterned as described above. For example, the different modifiers can cover the surface in an alternative pattern. On should appreciate that the support surface may be covered with a plurality of modifiers that are disposed on the surface to form a hydrophilic gradient. In some embodiments, each modifier has a different contact angle than the adjacent modifier. In some embodiments, the surface is partitioned with a plurality of different modifiers, the plurality of first modifiers being more hydrophilic than the at least one second modifier, the plurality of first modifiers having each a slightly different contact angle than the next first modifier. For example, the contact angle of each of the plurality of first modifier may differ by at least about 1°, 2°, 3°, 4°, 5°, 6°, 7°, 8°, 9°, 10°, 11°, 12°, 13°, 14°, 15°, 16°, 17°, 18°, 19°, 20°, 25°, 30° or more from that of the next first modifier. The plurality of first modifiers therefore forms a hydrophilic gradient and a predetermined path along which a droplet can be moved by surface-tension manipulation.

According to some aspects of the invention, the difference in surface contact angles between two different modifiers or a modifier and the non-modifier surface creates a virtual "wall". As used herein the term smaller contact angle (SCA) refers to the surface or modifier having smaller contact angle and the term higher contact angle (HCA) refers to the surface or modifier having higher contact angle. In the context of aqueous solutions, SCA are more hydrophilic than HCA. In some embodiments, HCA values are at least 20°, at least 30°, at least 35° higher than SCA. Accordingly, liquid volumes can be formed and isolated on such surfaces. For example, if the surface contact angle of the modifier is greater than the non-modifier surface contact angle, liquid volumes will form a droplet between two modifiers regions. One would appreciate that depending on liquid volume deposited onto the surface and the difference of contact values between modifiers, the droplet can occupy a single region of small contact angle (SCA) or multiple regions. For example, the liquid volume may occupy 1, 2, 3, 4, 5, 6, 7, 8, 9, 10, or more SCA regions. Accordingly, the liquid can occupy a footprint corresponding to one or more SCA. The footprint may then encompass one or more HCA. In some embodiments, to ensure that two droplets or small isolated volumes will not merge, liquid volumes are placed sufficiently apart from each others. For example, the spacing between two isolated volumes may comprise at least one, at least two, at least three, at least four, at least five, at least six, at least seven, at least eight, at least nine, at least ten HCA regions or modifiers regions. Placing the liquid volumes sufficiently apart also allows for keeping liquid volumes isolated during fluctuation of temperature such as during thermocycling. Because surface tension usually decreases with the increase of temperature, droplets may spread or move on the surface when the temperature of the support or of the liquid volume is raised. It will be appreciate that if the liquid volumes are kept sufficiently apart, liquid volumes will remain isolated and will not merge with adjacent liquid volumes during fluctuation of the temperature.

In one aspect of the invention, methods and devices are provided for processing independently one or more plurality of oligonucleotides in a temperature dependent manner at addressable features in isolated liquid volumes. In some embodiments, the method is conducted in a manner to provide a set of predefined single-stranded oligonucleotides or complementary oligonucleotides sequences for further specified reactions or processing. One should appreciate that each features being independently addressable, each reaction can be processed independently within a predefined isolated liquid volume or droplet on a discrete feature (e.g. virtual chamber). In some embodiments, the arrays are stored dry for subsequent reactions. In a preferred embodiment, support immobilized oligonucleotides can be hydrated independently with an aqueous solution. Aqueous solutions include but is not limited to water, buffer, primers, master mix, release chemicals, enzymes, or any combination thereof. Aqueous solution can be spotted or jetted onto specific surface location(s) corresponding to the discrete feature(s). Subsequently, miscible as well as non-miscible solution or aqueous gel can be deposited in the same fashion. Alternatively, a mechanical wave actuated dispenser can be used for transferring small volumes of fluids (e.g., picoliter or sub-picoliter). A mechanical wave actuated dispenser can be a piezoelectric inkjet device or an acoustic liquid handler. A piezoelectric inkjet device can eject fluids by actuating a piezoelectric actuation mechanism, which forces fluid droplets to be ejected. Piezoelectrics in general have good operating bandwidth and can generate large forces in a compact size. Some of the commercially available piezoelectric inkjet microarraying instruments include those from Perkin Elmer (Wellesley, Mass.), GeSim (Germany) and MicroFab (Plano, Tex.). Typical piezoelectric dispensers can create droplets in the picoliter range and with coefficient of variations of 3-7% Inkjetting technologies and devices for ejecting a plurality of fluid droplets toward discrete features on a substrate surface for deposition thereon have been described in a number of patents such as U.S. Pat. Nos. 6,511,849; 6,514,704; 6,042,211; 5,658,802, the disclosure of each of which is incorporated herein by reference.

In one embodiment, the fluid or solution deposition is performed using an acoustic liquid handler or ejector. Acoustic devices are non-contact dispensing devices able to dispense small volume of fluid (e.g. picoliter to microliter), see for example Echo 550 from Labcyte (CA), HTS-01 from EDC Biosystems. Acoustic technologies and devices for acoustically ejecting a plurality of fluid droplets toward discrete sites on a substrate surface for deposition thereon have been described in a number of patents such as U.S. Pat. Nos. 6,416,164; 6,596,239; 6,802,593; 6,932,097; 7,090,333 and US Patent Application 2002-0037579, the disclosure of each of which is incorporated herein by reference. The acoustic device includes an acoustic radiation generator or transducer that may be used to eject fluid droplets from a reservoir (e.g. microplate wells) through a coupling medium. The pressure of the focused acoustic waves at the fluid surface creates an upwelling, thereby causing the liquid to urge upwards so as to eject a droplet, for example from a well of a source plate, to a receiving plate positioned above the fluid reservoir. The volume of the droplet ejected can be determined by selecting the appropriate sound wave frequency.

In some embodiments, the source plate comprising water, buffer, primers, master mix, release chemicals, enzymes, or any combination thereof and the destination plates comprising the oligonucleotides or polynucleotides are matched up to allow proper delivery or spotting of the reagent to the proper site. The mechanical wave actuated dispenser may be coupled with a microscope and/or a camera to provide positional selection of deposited spots. A camera may be placed on both sides of the destination plate or substrate. A camera may be used to register to the positioning on the array especially if the nucleic acid is coupled with a fluorescent label.

One should appreciate that when manipulating small liquid volumes such as picoliters and nanoliters, the smaller the droplet, the faster it will evaporate. Therefore, aspects of the invention relate to methods and devices to limit, retard or prevent water or solvent evaporation. In some embodiments, the discrete features or a subset of discrete features can be coated with a substance capable of trapping or capturing water. In other embodiments, the water-trapping material can be spin-coated onto the support. Different materials or substances can be used to trap water at specific locations. For example, the water trapping substance may be an aqueous matrix, a gel, a colloid or any suitable polymer. In some embodiments, the material is chosen to have a melting point that allows it to remain solid or semi-solid (e.g. gel) at the reaction temperatures such as denaturing temperatures or thermocycling temperatures. Water trapping materials include but are not limited to colloidal silica, peptide gel, agarose, solgel and polydimethylsiloxane. In an exemplary embodiment, Snowtex® colloidal silica (Nissan Chemical) may be used. Snowtex colloidal silica is composed of monodispersed, negatively charged, amorphous silica particles in water. Snowtex colloidal silica can be applied as dry gel or as an hydrated gel onto the surface. In a preferred embodiment, the water trapping substance is spotted at discrete features comprising surface-bound oligonucleotides. Alternatively, oligonucleotides can be synthesized on the particles or nanoparticles (e.g. colloidal particles, Snowtex colloidal silica) and the particles or nanoparticles can be dispensed to the discrete features of the surface. In some embodiments, the water trapping substance is spotted on the discrete features of the support using a mechanical device, an inkjet device or an acoustic liquid handler.

One should appreciate, that evaporation can also be limited by forming a physical barrier between the surface of the droplet and the atmosphere. For example, a non-miscible solution can be overlaid to protect the droplet from evaporation. In some embodiments, a small volume of the non-miscible solution is dispensed directly and selectively at discrete location of the substrate such as features comprising a droplet. In some other embodiments, the non-miscible solution is dispensed onto a subset of features comprising a droplet. In other embodiments, the non-miscible solution is applied uniformly over the surface of the array forming a non-miscible bilayer in which the droplets are trapped. The non-miscible bilayer can then be evaporated to form a thin film over the surface or over a substantial part of the surface of the droplet. The non-miscible solution includes, but is not limited to, mineral oil, vegetable oil, silicone oil, paraffin oil, natural or synthetic wax, organic solvent that is immiscible in water or any combination thereof. One skilled in the art will appreciate that depending on the composition of the oils, some oils may partially or totally solidify at or below room temperature. In some embodiments, the non-miscible solution may be a natural or synthetic wax such as paraffin hydrocarbon. Paraffin is an alkane hydrocarbon with the general formula $C_nH_{2n+2}$. Depending on the length of the molecule, paraffin may appear as a gas, a liquid or a solid at room temperature. Paraffin wax refers to the solids with $20 \leq n \leq 40$ and has a typical melting point between about 47° C. to 64° C. Accordingly, in some embodiments, the support may be stored capped with a wax. Prior to use, heat may be applied to the support to allow the wax to turn into a liquid wax phase coating the support.

In some aspects of the invention, in subsequent steps, aqueous solution may be added to the droplet having a non-miscible solution at its surface. Solvent or aqueous solution may be added, for example, to initiate a reaction, to adjust a volume, to adjust a pH, to increase or decrease a solute concentration, etc. . . . . One would appreciate that the solvent or aqueous solution can penetrate the non-miscible layer using different mechanisms. For example, if using an inkjet head device, the aqueous solution is ejected and the physical momentum of the ejected droplet will enable the aqueous solution to cross the non-miscible layer. Other mechanisms may employ additional forces, such as for example magnetic and/or electrostatic forces and/or optical forces. The optical and magnetic forces can be created simultaneously or independently of one another. Furthermore, the mechanism can utilize coupled magneto-optical tweezers. In some embodiments, the aqueous solution to be dispensed contains magnetic nanoparticles and a magnetic force can be used to help penetration of the non-miscible layer. Alternatively, the aqueous solution carries an electrostatic charge and an external applied electric field can be used to achieve penetration of the non-miscible layer.

Yet, in another aspect of the invention, the size of the droplet is continuously or frequently monitored. One should appreciate that the size of the droplet is determined by the volume and by the surface tension of the solution. Accordingly, loss of volume can be detected by a decrease of the droplet footprint or radius of the droplet footprint. For example, using an optical monitoring system, through a microscope lens and camera system, the size or footprint of the droplet can be determined and the volume of the droplet can be calculated. In some embodiments, the volume of the droplet or the radius of the droplet is monitored every second or every millisecond. One would appreciate that the magnitude of the evaporation rate of the water from the droplet of interest depends in part on the temperature and thus increases with increasing temperatures. For example, during amplification by thermocycling or during denaturation of the double-stranded complexes, increase of temperature will result in the rapid evaporation of the droplet. Therefore, the volume of the droplet can be monitored more frequently and adjusting the droplet volume by re-hydration will be more frequent. In the event of volume fluctuation such as loss of volume, sub-pico to nano volumes of water or solvent can be dispensed onto the droplet or to the discrete feature comprising the droplet. Water or solvent volumes of about 0.5 pL, 1 pL, 10 pL, of about 100 pL, of about 1 nL, of about 10 nL, of about 100 nL can be dispensed this way. Water or solvent volumes may be delivered by any conventional delivery means as long that the volumes are controlled and accurate. In a preferred embodiment, water or solvent is dispensed using an inkjet device. For example, a typical inkjet printer is capable of producing 1.5 to 10 pL droplets, while other commercial ultrasonic dispensing techniques can produce 0.6 pL droplets. In some embodiments, water is added in a rapid series of droplets. In some embodiments, water is dispensed when registering a loss of volume of more than 10%, of more than 25%, of more than 35%, of more than 50%.

In other embodiment, evaporation rate is limited by raising the vapor rate or humidity surrounding the droplet. This can be performed, for example, by placing "sacrificial" droplets around or in close proximity to the droplet of interest (e.g. droplet comprising the oligonucleotides) (see for example, Berthier E. et al., Lab Chip, 2008, 8(6):852-859). In some embodiments, the surface or solid support is enclosed in a closed container to limit the evaporation.

Yet in another embodiment, the evaporation rate can be limited by adding a compound having a high boiling point component to the droplet(s) of interest, provided that the presence of the compound does not inhibit the enzymatic reactions performed on the substrate. The boiling point of a liquid is the temperature at which the liquid and vapor phases are in equilibrium with each other at a specified pressure. When heat is applied to a solution, the temperature of the solution rises until the vapor pressure of the liquid equals the pressure of the surrounding gases. At this point, vaporization or evaporation occurs at the surface of the solution. By adding a high boiling point liquid to the droplet of interest, evaporation of the water content of a droplet may be substantially reduced (see U.S. Pat. No. 6,177,558). In some embodiment, the high boiling point solution is a solvent. In some embodiments, the high boiling point liquid has a boiling point of at least 100° C., at least 150° C., at least 200° C. In some embodiments, glycerol is added to the solution, increasing the boiling point. Accordingly, the solution containing the high boiling point liquid will evaporate at a much slower rate at room temperature or at reaction conditions such as under thermocycling, extension, ligation and denaturation conditions.

Aspects of the invention provide methods for the amplification of one or more single-stranded oligonucleotide on the support. Oligonucleotides may be amplified before or after being detached from the support and/or eluted in a droplet. Preferably, the oligonucleotides are amplified on the solid support. One skilled in the art will appreciate that oligonucleotides that are synthesized on solid support will comprise a phosphorylated 3' end or an additional 3'-terminal nucleoside (e.g. T). The 3'-phosphorylated oligonucleotides are not suitable for polynucleotide assembly as the oligonucleotides cannot be extended by polymerase. In preferred aspects of the invention, the oligonucleotides are first amplified and the amplified products are assembled into a polynucleotide. Accordingly, aspect of the invention provides methods wherein a set or subset of oligonucleotides, that are attached to at a set of subset of features of the support, are amplified by locally delivering sub-microvolumes at addressable discrete features The term "amplification" means that the number of copies of a nucleic acid fragment is increased. As noted above, the oligonucleotides may be first synthesized onto discrete features of the surface, may be deposited on the substrate or may be deposited on the substrate attached to nanoparticles. In a preferred embodiment, the oligonucleotides are covalently attached to the surface or to nanoparticles deposited on the surface. In an exemplary embodiment, locations or features comprising the oligonucleotides to be amplified are first selected. In a preferred embodiment, the selected features are in close proximity to each others on the support. Aqueous or solvent solution is then deposited on the selected feature thereby forming a droplet comprising hydrated oligonucleotides. One would appreciate that each droplet is separated from the other by surface tension. In some embodiment the solution can be water, buffer or a solution promoting enzymatic reactions. In an exemplary embodiment, the solution includes, but is not limited to, a solution promoting primer extension. For example the solution may be composed of oligonucleotides primer(s), nucleotides (dNTPs), buffer, polymerase and cofactors. In other embodiments, the solution is an alkaline denaturing solution. Yet, in other embodiments, the solution may comprise oligonucleotides such as complementary oligonucleotides.

In some embodiments, oligonucleotides or polynucleotides are amplified within the droplet by solid phase PCR thereby eluting the amplified sequences into the droplet. In other embodiments, oligonucleotides or polynucleotides are first detached form the solid support and then amplified. For example, covalently-attached oligonucleotides are translated into surface supported DNA molecules through a process of gaseous cleavage using amine gas. Oligonucleotides can be cleaved with ammonia, or other amines, in the gas phase whereby the reagent gas comes into contact with the oligonucleotide while attached to, or in proximity to, the solid support (see Boal et al., NAR, 1996 (24(15):3115-7), U.S. Pat. Nos. 5,514,789; 5,738,829 and 6,664,388). In this process, the covalent bond attaching the oligonucleotides to the solid support is cleaved by exposing the solid support to the amine gas under elevated pressure and/or temperature. In some embodiments, this process may be used to "thin" the density of oligonucleotides at specific features. One skilled in the art will appreciate that DNA microarrays can have very high density of oligonucleotides on the surface (approximately $10^8$ molecules per feature), which can generate steric hindrance to polymerases needed for PCR. Theoretically, the oligonucleotides are generally spaced apart by about 2 nm to about 6 nm. For polymerases, a typical 6-subunit enzyme can have a diameter of about 12 nm. Therefore the support may need to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligonucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represents an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

According to aspects of the invention, hydrated oligonucleotides can be amplified within the droplet, the droplet acting as a virtual reaction chamber. In some embodiments, the entire support or array containing the discrete features is subjected to amplification. In other embodiments, one or more selected discrete features are subjected to amplification.

Amplification of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from wide spectrum (100 nm to 100,000 nm, i.e. from ultraviolet to infrared). In some embodiments, the feature on which the droplet is spotted comprises an optical absorber or indicator. In some other embodiment, optical absorbent material can be added on the surface of the droplet. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. Yet in another embodiment, the whole support can be heated and cooled down to allow enzymatic reactions to take place. One method to control the temperature of the surface droplets is by using a scanning optical energy deposition setup. An energy source can be directed by a scanning setup to deposit energy at various locations on the surface of the solid support comprising attached or supported molecules. Optical absorbent material can be added on the surface of the solid support or on the surface of droplet.

Optical energy source, such as a high intensity lamp, laser, or other electromagnetic energy source (including microwave) can be used. The temperature of the different reaction sites can be controlled independently by controlling the energy deposited at each of the features.

For example, a Digital Micromirror Device (DMD) can be used for temperature control. DMD is an optical semiconductor. See, for example, U.S. Pat. No. 7,498,176. In some embodiments, a DMD can be used to precisely heat selected features or droplets on the solid support. The DMD can be a chip having on its surface several hundred thousand microscopic mirrors arranged in a rectangular array which correspond to the features or droplets to be heated. The mirrors can be individually rotated (e.g., ±10-12°), to an on or off state. In the on state, light from a light source (e.g., a bulb) is reflected onto the solid support to heat the selected spots or droplets. In the off state, the light is directed elsewhere (e.g., onto a heatsink). In one example, the DMD can consist of a 1024× 768 array of 16 μm wide micromirrors. These mirrors can be individually addressable and can be used to create any given pattern or arrangement in heating different features on the solid support. The features can also be heated to different temperatures, e.g., by providing different wavelength for individual spots, and/or controlling time of irradiation.

One would appreciate that amplification occurs only on features comprising hydrated template oligonucleotides (i.e. local amplification at features comprising a droplet). Different set of features may be amplified in a parallel or sequential fashion with parallel or sequential rounds of hydrating (i.e. dispensing a droplet on a specific feature), amplifying oligonucleotides and drying the set of features. In some embodiments, the support is dried by evaporating liquid in a vacuum while heating. Thus, after each round of amplification, the support will comprise a set of droplets containing oligonucleotides duplexes. The complementary oligonucleotides can be released in solution within the droplet and be collected. Alternatively, complementary oligonucleotides may be dried onto the discrete features for storage or further processing. Yet, complementary oligonucleotides can be subjected to further reactions such as error filtration or assembly. In some embodiments, a different set or subset of features can then be hydrated and a different set or subset of template oligonucleotides can be amplified as described herein. For example, a droplet can be dispensed (e.g., inkjetted) on a support. The droplet can contain various reagents such as enzymes, buffers, dNTPs, primers, etc. The droplet covers a discrete feature (a feature corresponds to a predefined sequence) on the support. PCR can be carried out to synthesize oligonucleotides complementary to template oligonucleotides that are attached to the feature. In the case of the enzymatic amplification, the solution includes but is not limited to primers, nucleotides, buffers, cofactors, and enzyme. For example, an amplification reaction includes DNA polymerase, nucleotides (e.g. dATP, dCTP, dTTP, dGTP), primers and buffer.

In some embodiments, the oligonucleotides may comprise universal (common to all oligonucleotides), semiuniversal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially.

In some embodiments, primers/primer binding site may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide. In some embodiments, after amplification, the pool of nucleic acids may be contacted with one or more endonucleases to produce double-stranded breaks thereby removing the primers/primer binding sites. In certain embodiments, the forward and reverse primers may be removed by the same or different restriction endonucleases. Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, T4 DNA polymerase, CEL I nuclease, etc.) may be used to produce blunt ends. Alternatively, the sticky ends formed by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

In some embodiments, the primer is a primer containing multiple uracil (U). The primer is first annealed to a support-bound single-stranded oligonucleotide and extended with the addition of dNTPs and an appropriate polymerase under appropriate conditions and temperature. In a subsequent step, the primer is removed. In some embodiments, uracil DNA glycosylase (UDG) may be used to hydrolyze a uracil-glycosidic bond in a nucleic acid thereby removing uracil and creating an alkali-sensitive a basic site in the DNA which can be subsequently hydrolyzed by endonuclease, heat or alkali treatment. As a result, a portion of one strand of a double-stranded nucleic acid may be removed thereby exposing the complementary sequence in the form of a single-stranded overhang. This approach requires the deliberate incorporation of one or more uracil bases on one strand of a double-stranded nucleic acid fragment. This may be accomplished, for example, by amplifying a nucleic acid fragment using an amplification primer that contains a 3' terminal uracil. After treatment with UDG, the region of the primer 5' to the uracil may be released (e.g., upon dilution, incubation, exposure to mild denaturing conditions, etc.) thereby exposing the complementary sequence as a single-stranded overhang. It should be appreciated that the length of the overhang may be determined by the position of the uracil on the amplifying primer and by the length of the amplifying primer. In some embodiments, mixture of Uracil DNA glycosylase (UDG) and the DNA glycosylase-lyase Endonuclease VIII, such as USER™ (Uracil-Specific Excision Reagent) is used. UDG catalyses the excision of a uracil base, forming an abasic site while leaving the phosphodiester backbone intact. The lyase activity of Endonuclease VIII breaks the phosphodiester backbone at the 3' and 5' sides of the abasic site so that base-free deoxyribose is released.

After amplification, the polymerase may be deactivated to prevent interference with the subsequent steps. A heating step (e.g. high temperature) can denature and deactivate most enzymes which are not thermally stable. Enzymes may be deactivated in presence (e.g. within the droplet) or in the absence of liquid (e.g. dry array). Heat deactivation on a dry support has the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

In some embodiments, discrete features may contain oligonucleotides that are substantially complementary (e.g. 50%, 60%, 70%, 80%, 90%, 95%, 98%, 99% or 100%). Template oligonucleotides can have inherent errors as they are generally chemically synthesized (e.g., deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wide-type sequence of a gene of interest). For example, a template oligonucleotide can contain an error which can be a mismatch, deletion, or insertion. In PCR synthesis, the error is retained in the synthesized oligonucleotide. Additional errors can be introduced during PCR reactions. Accordingly, methods for error correction are needed for high-fidelity gene synthesis/assembly.

Accordingly, some aspects of the invention relate to the recognition and local removal of double-stranded oligonucleotides containing sequence mismatch errors at specific features. In one preferred embodiment of the invention, mismatch recognition can be used to control the errors generated during oligonucleotide synthesis, gene assembly, and the construction of longer polynucleotides. After amplification, the totality of the features or a set of the features comprising oligonucleotide duplexes are first subjected to round(s) of melting and annealing as described above. In a preferred aspect of the invention, oligonucleotides having predefined sequences are assembled after being amplified and error-filtered. In some embodiments, two adjacent droplets containing two multiple copies of different oligonucleotides or polynucleotides in solution are combined by merging the appropriate droplets on the solid support. The solid support comprises different and unique molecules supported or attached to the surface, a unique molecule supported or attached to the surface at multiple positions other unique molecules supported or attached to the surface. On the solid support surface an existing pattern of molecules can be found. Different molecules or oligonucleotides can exist at different positions. One should appreciate that the arrangement of these unique molecules can be designed to strategically allow the subsequent combining of the contents of these sites. For example, these unique molecules can be arranged in a checker board pattern.

Figure 5A:
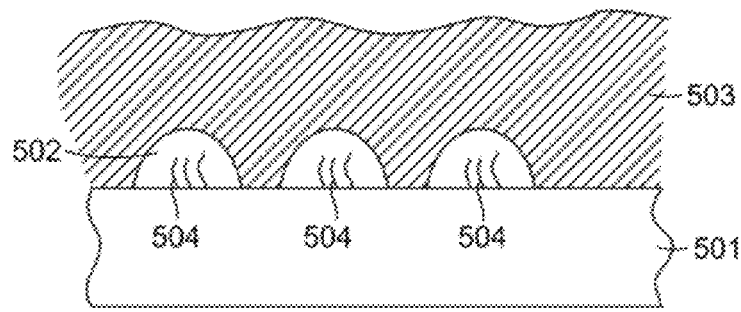
FIG. 5A illustrates micro-volumes (502) suitable for shuffling and covered by a blanket of fluid (503).
Figure 5B:
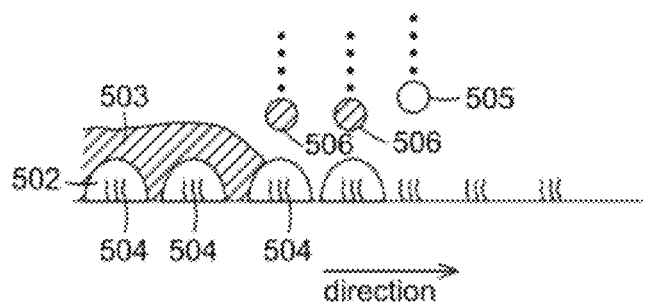
FIG. 5B illustrates a process for the creation of micro-volumes in a serial manner according to one embodiment.

Aspect of the invention also relate to methods to shuffle molecules within one or more features of a high diversity library on a solid support. Various fluidic methods can be used to achieve shuffling. In some embodiments, shuffling can be performed with deposited micro-volumes or without micro-volumes. For example, with reference to FIG. 5, shuffling can be implemented in individual micro-volumes (502) created at the deposition of one or more fluids. Members of the high diversity library (504) can be immobilized on a surface (501). Shuffling can be achieved by heating and cooling the micro-volumes (502), causing localized melting and reannealing at each location where a member of the library is positioned (FIG. 5A). These micro-volumes can be created in a serial manner as illustrated in FIG. 5B showing a process progressing from right to left. For each member of the library, first, a liquid suitable for the shuffling reaction is deposited (505), resulting in micro-volumes (502); following the deposition of (505), a second fluid (506) that is immiscible to (505) is deposited over the micro-volumes (502), forming a blanket (503) over the micro-volumes (502). This process can be carried out until all the desirable members of the high diversity library (504) are covered by micro-volume (502) and/or blanket (503).

Figure 2:
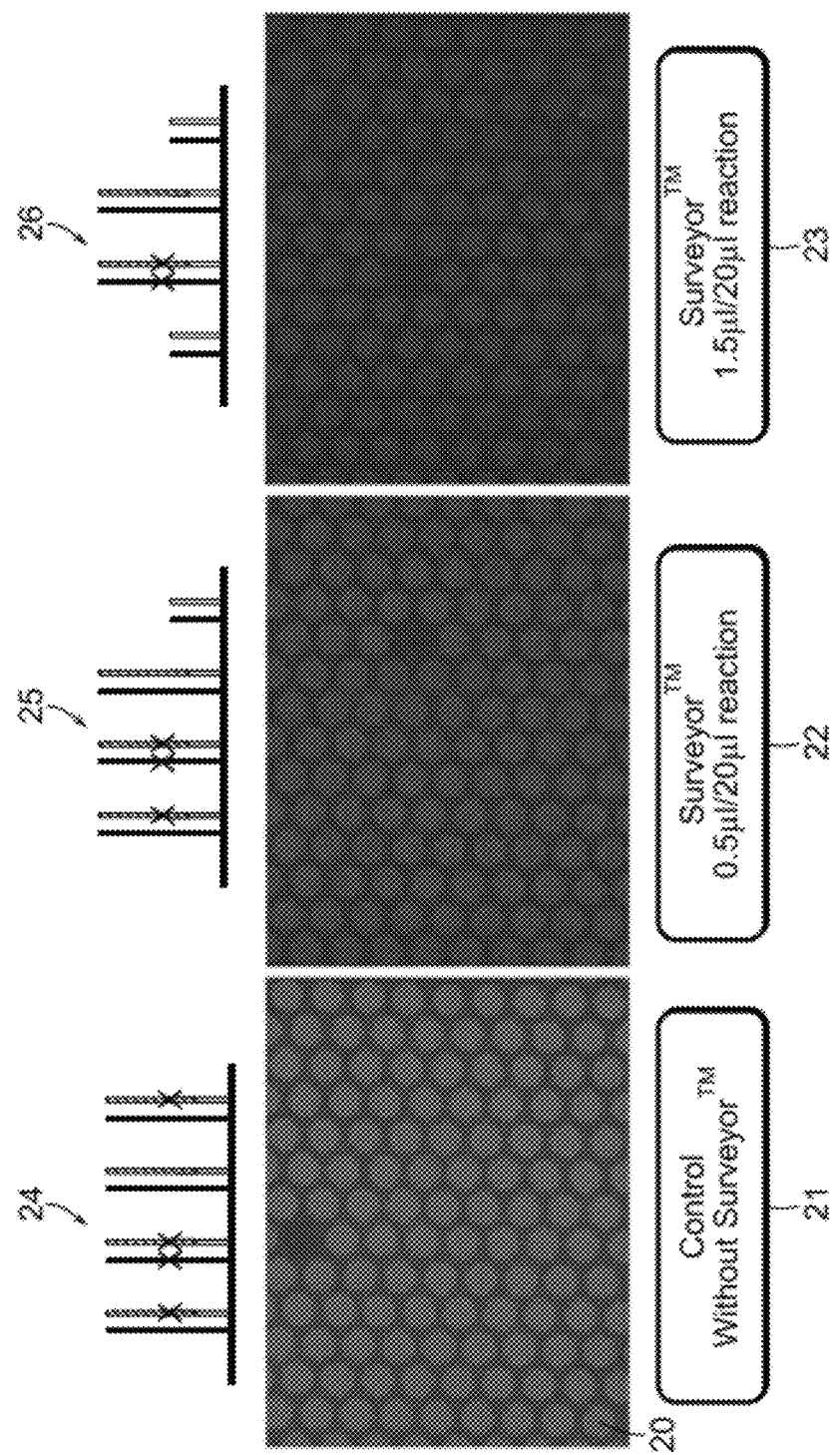
FIG. 2 shows an exemplary Surveyor cleavage experiment of heteroduplexes after shuffling.
Figure 5C:
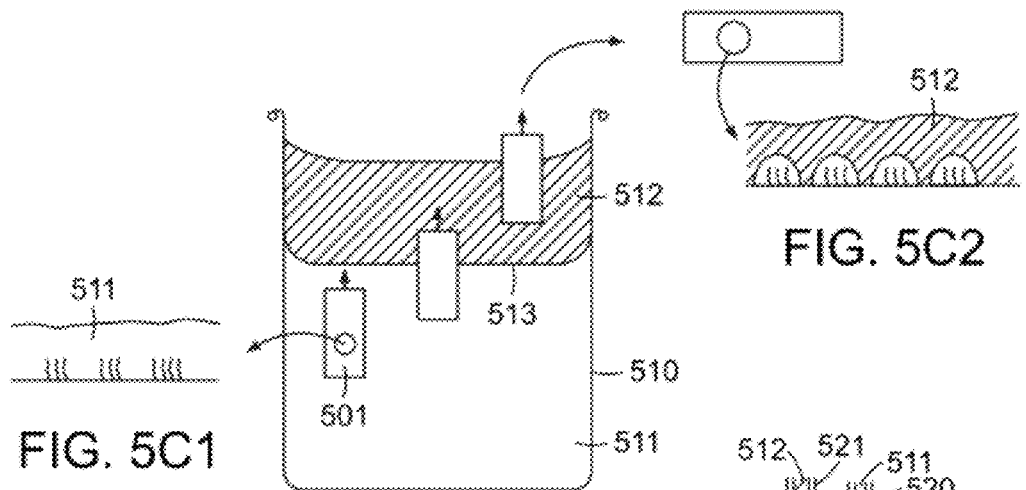
FIG. 5C illustrates a process for the creation of micro-volumes according to another embodiment.

In another example, the surface properties of the substrate (501) can be utilized to achieve the structure in FIG. 5A on a global scale. As illustrated in FIG. 5C, the substrate (501) starts fully immersed in a fluid (511) contained in a container (510), such that all the members of the high diversity library are in contact with the fluid (511), as shown in FIG. 5C1. The fluid (511) is such that it has low contact angle with the substrate surface where the members of the library resides. A second fluid (512) is added to the container (510) which is immiscible to the first fluid (511), forming an interface (513). The second fluid (512) is such that it has a different contact angle (preferably higher) with the substrate surface where the members of the library resides. Yet, between the members of the library, the second fluid (512) may have a lower contact angle to the surface. When the substrate is moved from being fully immersed in (511) through the interface (513), small volumes of the first fluid (511) is retained on the surface of the substrate (510) where the members of the high diversity library resides, forming micro-volumes (504). Furthermore, once the surface passes the interface (513), the micro-volumes are covered by a blanket formed by fluid (512). The resulting structure of the micro-volumes is shown in FIG. 5C2.

Figure 5D:
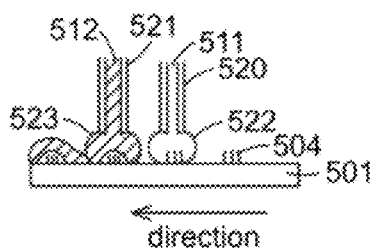
FIG. 5D illustrates a process for the creation of micro-volumes according to another embodiment.

The process illustrated in FIG. 5C can be carried out without the container (510) by using an arrangement shown in FIG. 5D. Two meniscus capillary heads (520, 512) are lowered to near contact with the substrate (501). Fluids (511) and (512) are supplied into the meniscus capillary heads (520, 521) to form a small volume (522, 523) that contacts both the meniscus capillary heads (520, 521) and the substrate (501). The relative motion of the heads and the substrate is shown in the direction of the arrow. The volumes (522, 523) may be placed close enough to form an interface, or separated enough to from a space between the volumes. Micro-volumes are created as the members of the library (504) passes under first the reaction fluid meniscus (522) then the blanket fluid meniscus (523), resulting in the encapsulated features as shown in FIG. 5A.

Shuffling can also be achieved without micro-volumes. In one example, as outlined in FIG. 6, the precise control of short periods of time for which temperature of the substrate (601) and fluid (600) is raised to cause melting is used to achieve localized melting and reannealing through diffusion limit. FIG. 6A1 shows the setting prior to melting, where homoduplexes (602, 603) are attached to the surface via the covalent bond of the template strand. When temperature is raised to above the melting temperature of the homo-duplexes, melting takes place and the single stranded copies (604, 605) are released into the fluid (600). FIG. 6B1 shows the melting at a time immediately after the temperature increases, and FIG. 6C1 shows the melting at a later time than that of FIG. 6B1, and FIG. 6D1 shows the melting at a later time than that of FIG. 6C1. The melted single strand copies (604, 605) diffuse away from their original location and the diffusion is governed by the diffusion equation. FIGS. 6A2, 6B2, 6C2, and 6D2 are intended to illustrate the diffusion process as time progresses by showing the concentration of duplexes (e.g., signal strength) at two adjacent positions on the substrate (601). The longer the time is allowed for diffusion, the further the molecules would travel. The characteristic diffusion distance ($L_d$) is related to the diffusion coefficient (D) and time (t):

$$L_d = \mathrm{sqrt}(4Dt)$$

The time that is allowed for diffusion can be controlled, and thus the characteristic diffusion distance can be controlled also, since the diffusion coefficient is determined by the molecular species. As shown in FIG. 6E, when reannealing is induced (by lowering temperature) after a brief period of melting time, the reannealed heteroduplexes are recaptured back to the original positions (606, 607), achieving a shuffling operation. If the melting time is allowed to proceed longer, more of the molecules (608) will diffuse away into the bulk of the fluid (600) and will be less likely to be recaptured back to the original position.

Figure 7A:
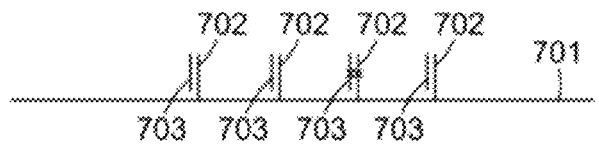
FIG. 7A illustrates homoduplexes formed by the template (702) and copies (703) on a surface (701).
Figure 7B:
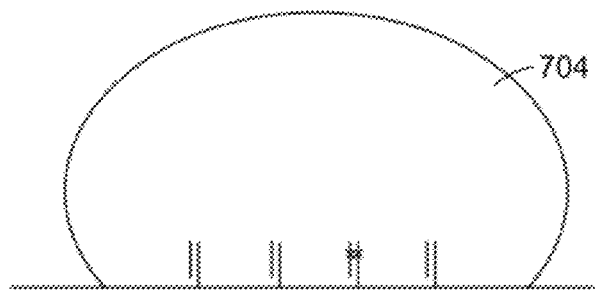
FIG. 7B illustrates the homoduplexes covered by a volume (704).
Figure 7C:
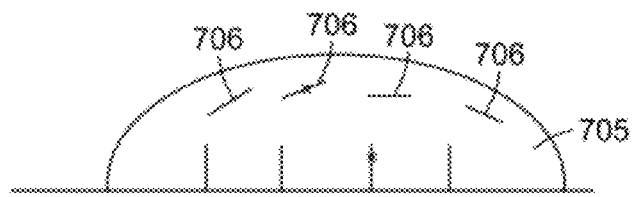
FIG. 7C illustrates the melted copies (706) in the fluid (705) which is reduced in volume.
Figure 7D:
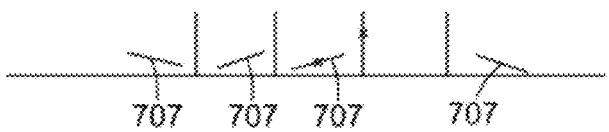
FIG. 7D illustrates an embodiment in which the droplet is allowed to completely dry, depositing the copies (707) on the surface.
Figure 7E:
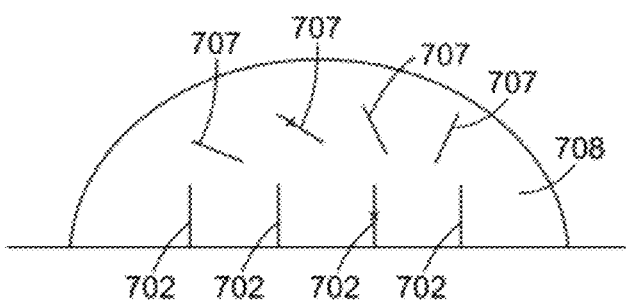
FIG. 7E shows the substrate after rehydration to resuspend the copies (707) into the fluid volume (708).

In some embodiments, shuffling can be achieved with a droplet that is actively evaporating. In the example shown in FIG. 7, the surface (701) is first raised to a temperature above the melting temperature of the homo-duplexes formed by the template (702) and copies (703, FIG. 7A). A volume (704) is deposited to cover the homo-duplexes (FIG. 7B), and since the surface is already at the high melting temperature, the copies are melted (706) into the fluid (705) which is reducing in volume rapidly due to evaporation (FIG. 7C). The droplet is allowed to completely dry, depositing the copies (707) onto the surface (FIG. 7D). The substrate is then cooled to below the melting temperature of the particular population, and rehydrated to resuspend the copies (707) into the fluid volume (708, FIG. 7E). Subsequent reannealing of the copies (707) to the templates (702) results in a shuffled heteroduplex group, completing the shuffling operation.

Following melting and reannealing, heteroduplexes can be removed by various methods described above. The remaining duplexes can then be subject to melting again to denature some or all of the duplexes. In some embodiments, some duplexes (e.g., the cleaved or truncated duplexes) are selectively melted, leaving others (e.g., the full-length duplexes) intact. The conditions for such stringent melt (e.g., a precise melting temperature) can be determined by observing a real-time melt curve. In an exemplary melt curve analysis, PCR products are slowly heated in the presence of double-stranded DNA (dsDNA) specific fluorescent dyes (e.g., SYBR Green, LCGreen, SYTO9 or EvaGreen). With increasing temperature the dsDNA denatures (melts), releasing the fluorescent dye with a resultant decrease in the fluorescent signal. The temperature at which dsDNA melts is determined by factors such as nucleotide sequence, DNA length and GC/AT ratio. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available and may be in which G-C stacking interactions, solvent effects, the desired assay temperature and the like are taken into account. Melt curve analysis can detect a single base difference. Various methods for accurate temperature control at individual features can be used as disclosed above.

Some aspects of the invention relate to destination selection and routing of the isolated volumes and therefore to the control of the location or footprint of merged volumes. One would appreciate that as individual regions of the support are addressable, individual isolated volumes such as droplets may be controlled individually. In some embodiments, it is preferable to place isolated volumes onto adjacent regions or features to allow merging of the volumes. Yet, in other embodiments, isolated volumes are directed or routed to a selected destination. In some embodiments, the substrate of the support is substantially planar and droplets are routed using a two-dimensional path (e.g. x,y axis). Droplets may be moved to bring them to selected locations for further processing, to be merged with a second isolated volume into a second stage droplet at preselected locations and/or during the transport, to remove some reactants from the droplet (referred as. "wash-in-transport' process, as described herein) etc.

In some embodiments, step-wise hierarchical and/or sequential assembly can be used to assemble oligonucleotides and longer polynucleotides. In a preferred embodiment, the methods use hierarchical assembly of two or more oligonucleotides or two or more subassemblies polynucleotide fragments at a time. Neighboring droplets can be manipulated (move and/or merged, as described above) to merge following a hierarchical strategy thereby improving assembly efficiency. In some embodiments, each droplet contains oligonucleotides with predefined and different nucleic acid sequences. In some embodiments, two droplets are moved following a predefined path to an oligonucleotide-free position. In a preferred embodiment, the assembly molecules (e.g. oligonucleotides) are pre-arranged on the support surface at pre-determined discrete features. One should appreciate that isolated volumes may be routed independently in a sequential or highly parallel fashion. Droplets may be routed using electrowetting-based techniques (see for example, U.S. Pat. No. 6,911,132 and U.S. Patent Application 2006/0054503). Electrowetting principle is based on manipulating droplets on a surface comprising an array of electrodes and using voltage to change the interfacial tension. In some embodiments, droplets are moved using a wettability gradient. It has been shown that droplets placed on wettability gradient surfaces typically move in the direction of increasing wettability (see Zielke and Szymczyk, Eur. Phys. J. Special Topics, 166, 155-158 (2009)). In other embodiments, droplets may be moved using a thermal gradient. When placed on a thermal gradient, droplets move from higher temperature locations towards lower temperature locations. Moving droplets using electrowetting, temperature gradients and wettability gradients depend on the liquid (e.g. aqueous, non-aqueous, solute concentration), the size of the droplets and/or the steepness of the gradient.

Another benefit of the move operation described herein is the implementation of a "wash" operation. The movement of the liquid away from a surface feature allows the separation of the surface-bound molecules (e.g. oligonucleotides) from the molecules in solution. Hence, a wash operation is therefore implemented. For example, wash-in-transportation can be used to remove the template oligonucleotides form the complementary oligonucleotides after amplification. In some embodiments, "wash-in transportation" features or wash spots may be placed adjacent to features where oligonucleotide processing takes place. Wash spots can be placed adjacent to the features. Undesirable products released in the droplet solution on the features can be moved to the wash spots respectively. In some embodiments, the support provides one wash spot for each assembly feature or a common wash spot for two or more assembly features. Wash-in-transportation process can also be used to remove unwanted error-containing oligonucleotides from stable duplexes after annealing and stringent melt. For example, stringent melt features can be placed along the path of assembly progression, allowing for stringent melt error correction as described above. Similarly, the support may comprise one SM spot for each assembly step or a common SM spot for two or more assembly features.

In some embodiments, the content of two microvolumes such as droplets are merged to allow for polynucleotide assembly. For example, two first stage droplets can be merged forming a larger second stage droplet. In some embodiments, "merger" droplets or "anchor" droplets are added which may contain or not contain enzyme (e.g. polymerase, ligase, etc.), additional oligonucleotides and all reagents to allow assembly by PCR or by ligation (enzymatic or chemical) or by any combination of enzymatic reaction. For example, oligonucleotides in a given droplet may hybridize to each other and may assemble by PCR or ligation. The merged droplets or second stage droplets contain polynucleotides subassemblies and can be subsequently merged to form larger droplets or third stage droplet containing larger fragments. As used herein the term subassembly refers to a nucleic acid molecule that has been assembled from a set of oligonucleotides. Preferably, a subassembly is at least 2-fold or more long than the oligonucleotides. For example, a subassembly may be about 100, 200, 300, 400, 500, 600, or ore bases long. One should appreciate that the use of droplets as isolated reaction volume enables a highly parallel system. In some embodiments, at least 100, at least 1,000 reactions can take place in parallel. In some embodiments, the primers are immobilized on the support in close proximity to the spots containing the oligonucleotides to be assembled. In some embodiments, the primers are cleaved in situ. In some embodiments, the primers are supported on the solid support. The primers may then be cleaved in situ and eluted within a droplet that will subsequently merged with a droplet containing solid supported or eluted oligonucleotides.

In certain embodiments, the oligonucleotides are designed to provide the full sense (plus strand) and antisense (minus strand) strands of the polynucleotide construct. After hybridization of the plus and minus strand oligonucleotides, two double-stranded oligonucleotides are subjected to ligation in order to form a first subassembly product. Subassembly products are then subjected to ligation to form a larger nucleic acid or the full nucleic acid sequence.

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands at a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photo-chemical ligation reactions. It should be appreciated that in some embodiments chemical ligation can be used to produce naturally occurring phosphodiester internucleotide linkages, non-naturally-occurring phosphamide pyrophosphate internucleotide linkages, and/or other non-naturally-occurring internucleotide linkages.

In some embodiments, the process of chemical ligation may involve one or more coupling agents to catalyze the ligation reaction. A coupling agent may promote a ligation reaction between reactive groups in adjacent nucleic acids (e.g., between a 5'-reactive moiety and a 3'-reactive moiety at adjacent sites along a complementary template). In some embodiments, a coupling agent may be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation may be an autoligation reaction that does not involve a separate coupling agent. In autoligation, the presence of a reactive group on one or more nucleic acids may be sufficient to catalyze a chemical ligation between nucleic acid termini without the addition of a coupling agent (see, for example, Xu et al., (1997) Tetrahedron Lett. 38:5595-8). Non-limiting examples of these reagent-free ligation reactions may involve nucleophilic displacements of sulfur on bromoacetyl, tosyl, or iodo-nucleoside groups (see, for example, Xu et al., (2001) Nat. Biotech. 19:148-52). Nucleic acids containing reactive groups suitable for autoligation can be prepared directly on automated synthesizers (see, for example, Xu et al., (1999) Nuc. Acids Res. 27:875-81). In some embodiments, a phosphorothioate at a 3' terminus may react with a leaving group (such as tosylate or iodide) on a thymidine at an adjacent 5' terminus. In some embodiments, two nucleic acid strands bound at adjacent sites on a complementary target strand may undergo autoligation by displacement of a 5'-end iodide moiety (or tosylate) with a 3'-end sulfur moiety. Accordingly, in some embodiments the product of an autoligation may include a non-naturally-occurring internucleotide linkage (e.g., a single oxygen atom may be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid may be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid may be ligated in a separate reaction containing phosphorylated oligonucleotides corresponding to the strand that is to be ligated and non-phosphorylated oligonucleotides corresponding to the complementary strand. The non-phosphorylated oligonucleotides may serve as a template for the phosphorylated oligonucleotides during a chemical ligation (e.g., using cyanogen bromide). The resulting single-stranded ligated nucleic acid may be purified and annealed to a complementary ligated single-stranded nucleic acid to form the target duplex nucleic acid (see, for example, Shabarova et al., (1991) Nucl. Acids Res. 19:4247-51).

In one aspect, a nucleic acid fragment may be assembled in a polymerase mediated assembly reaction from a plurality of oligonucleotides that are combined and extended in one or more rounds of polymerase-mediated extensions. In some embodiments, the oligonucleotides are overlapping oligonucleotides covering the full sequence but leaving single-stranded gaps that may be filed in by chain extension. The plurality of different oligonucleotides may provide either positive sequences (plus strand), negative sequences (minus strand), or a combination of both positive and negative sequences corresponding to the entire sequence of the nucleic acid fragment to be assembled. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 5 and about 500 oligonucleotides long (e.g., between about 10 and 100, between about 10 and 75, between about 10 and 50, about 20, about 25, about 30, about 35, about 45, about 50, etc.). However, shorter, longer, or intermediate overlapping lengths may be used. It should be appreciated that overlaps between different input nucleic acids used in an assembly reaction may have different lengths.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentRO (exo–) DNA Polymerase (thermophilic DNA polymerases with or without a 3'→5' exonuclease/proofreading activity from *Thermococcus litoralis*; also known as Th polymerase); Deep VentR® DNA Polymerase and Deep VentR® (exo–) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus kodakaraensis* KODI DNA polymerase with a 3'→5' exonuclease/proofreading activity, available from Novagen,); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of *Methanopyrus* topoisomerase, with no exonuclease activity, available from Fidelity Systems); TopoTaq HiFi which incorporates a proofreading domain with exonuclease activity; Phusion™ (a *Pyrococcus*-like enzyme with a processivity-enhancing domain, available from New England Biolabs); any other suitable DNA polymerase, or any combination of two or more thereof.

In some embodiments, the polymerase can be a SDP (strand-displacing polymerase; e.g, an SDPe—which is an SDP with no exonuclease activity). This allows isothermal PCR (isothermal extension, isothermal amplification) at a uniform temperature. As the polymerase (for example, Phi29, Bst) travels along a template it displaces the complementary strand (e.g., created in previous extension reactions). As the displaced DNAs are single-stranded, primers can bind at a consistent temperature, removing the need for any thermocycling during amplification, thereby avoiding or decreasing evaporation of the reaction mixture.

It should be appreciated that the description of the assembly reactions in the context of the oligonucleotides is not intended to be limiting. For example, other polynucleotides (e.g. single-stranded, double-stranded polynucleotides, restriction fragments, amplification products, naturally occurring polynucleotides, etc.) may be included in an assembly reaction, along with one or more oligonucleotides, in order to generate a polynucleotide of interest.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Mismatch Cleavage and Removal Using Surveyor™

Figure 3:
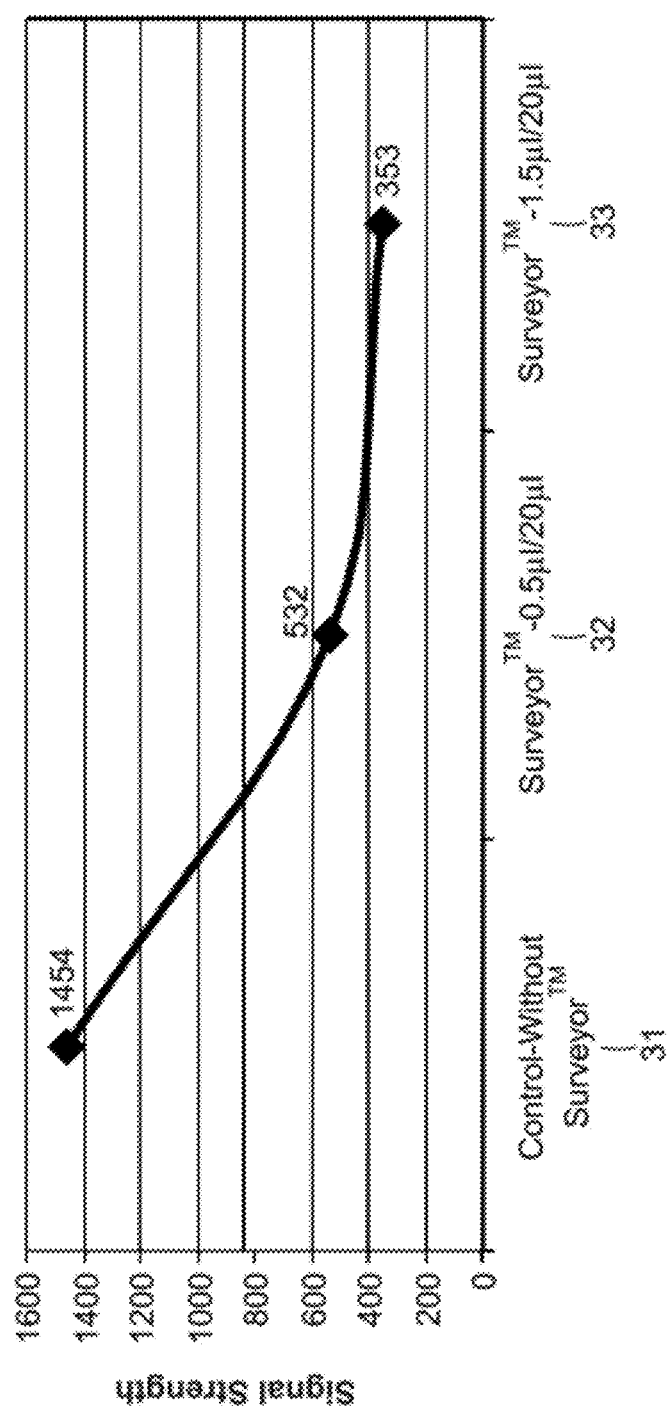
FIG. 3 shows an exemplary graph showing Microarray Spot Intensity (signal strength) after Surveyor™ treatment.

An example of mismatch cleavage and removal is shown in FIGS. 2 and 3. With reference to FIG. 2, microarray spots 20 were subject to labeling with in 0.005% Triton X-100, mM Tris-HCl (pH 7.4), 5 mM MgCl2, 7.5 mM dithiothreitol (DTT), 0.4 mM dATP, 0.4 mM dGTP, 0.4 mM dTTP, 4 µM Cy3CdCTP, 0.4 uµM of universal primer, 0.04 U/µl of Klenow fragment DNA polymerase exo– at 37° C. for 60 minutes. In the control experiment (left panel), shuffled microarray 21 received no enzymatic treatment. The center panel shows shuffled microarray 22 that received 0.5 µl Surveyor™ per 20 µl reaction volume. The right panel is shuffled microarray 23 that received 1.5 µl Surveyor™ per 20 ul reaction volume. 24, 25, and 16 are schematic representation of shuffled microarray 21, 22, and 23, respectively.

The image of shuffled microarray 21 is the brightest, suggesting that the most amount of Cy3 dye remained on the shuffled microarray 21 than 22 and 23. This is further substantiated by directly measuring the Cy3 signal strength on shuffled microarray 21, 22, and 23. With reference to FIG. 3, reference numbers 31, 32, and 33 correspond to the average spot intensity of shuffled microarray 21, 22, and 23, respectively. Therefore, Surveyor™ treatment effectively removed mismatch-containing duplexes, resulting in lesser amount of Cy3 signals.

Example 2

Production of High Fidelity Oligonucleotides Using Surveyor™ Cleavage

Figure 4:
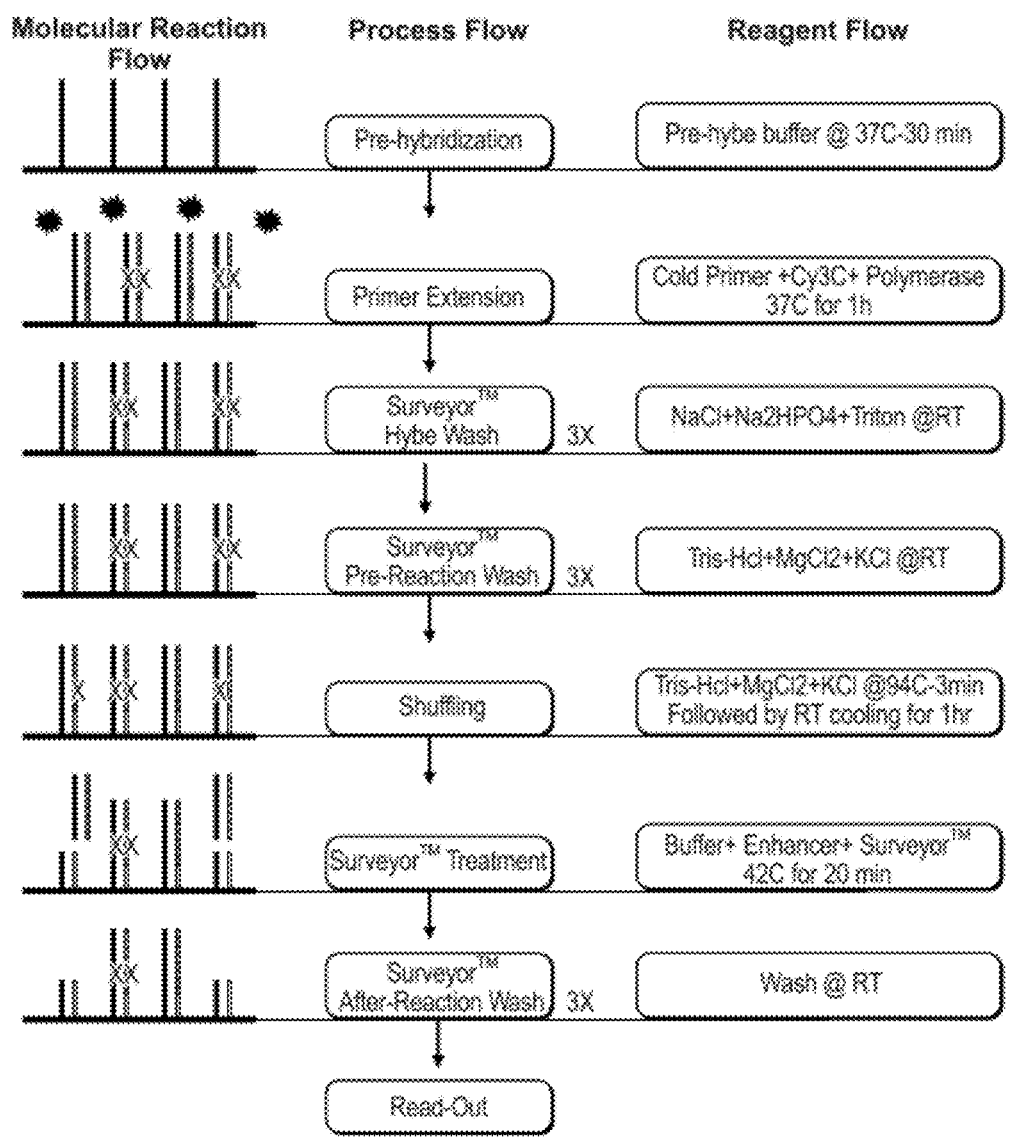
FIG. 4 illustrates an exemplary method for producing high fidelity oligonucleotides using Surveyor cleavage: molecular reaction flow, process flow, and reagent flow.

Exemplary molecular reaction flow, process flow, and reagent flow for producing high fidelity oligonucleotides using Surveyor™ cleavage are shown in FIG. 4. Seven (7) steps were used in this example.

Step 1: Chip Prehybridization. Microarray was prehybridized with 0.005% Triton X-100, 0.2 mg/ml acytylated Bovine Serum Albumin, 10 mM Tris-HCl (pH 7.4), 5 mM MgCl2, 7.5 mM dithiothreitol (DTT) at 37° C. for 30 minutes.

Step 2: Primer Extension. Complementary strands on the chip were synthesized in 0.005% Triton X-100, 10 mM Tris-HCl (pH 7.4), 5 mM MgCl2, 7.5 mM dithiothreitol (DTT), 0.4 mM dNTPs, 0.4 µM of universal primer, 0.04 U/µl of Klenow fragment DNA polymerase exo– at 37° C. for 60 minutes.

Step 3: Surveyor™ hybe wash. Unincorporated nucleotides were removed with 0.9M NaCl, 60 mM NaH2PO4 and 0.005% Triton X-100. Chip was washed in Surveyor™ hybe buffer three times at room temperature.

Step 4: Surveyor™ reaction wash. Chip was washed in Surveyor™ reaction buffer three times at room temperature. Composition of Surveyor™ reaction buffer: 20 mM Tris-HCl (pH 7.4), 10 mM MgCl2 and 25 mM KCl.

Step 5: Shuffling. The chip was heated to 94° C. in a Surveyor™ reaction buffer for 3 minutes for DNA melting followed by room temperature incubation for 60 minutes for heteroduplex formation.

Step 6: Surveyor™ treatment. The Surveyor™ reaction buffer from step 5 was removed and the chip was treated with Surveyor™/enhancer in 20 mM Tris-HCl (pH 7.4), 10 mM MgCl2 and 25 mM KCl and incubated at 42° C. for 20 minutes. Two different concentrations of Surveyor™/enhancer were used: 1). 0.5 µl/20 µl reaction and 1.5 µl/20 µl reaction. Surveyor™ and enhancer were used in equal volumes.

Step 7: Surveyor™ after reaction wash. Chip was washed with 0.9M NaCl, 60 mM NaH2PO4, 0.005% Triton X-100 and 6 mM EDTA for three times at room temperature to remove cleaved error-prone heteroduplexes.

EQUIVALENTS

The present invention provides among other things novel methods and devices for high-fidelity gene synthesis and assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT application PCT/US09/55267, now International Publication No. WO2010/025310; to PCT application PCT/US 2010/055298, now International Publication No. WO2011/056872; and to U.S. Provisional application 61/264,632 filed on Nov. 25, 2009. All publications, patents and sequence database entries mentioned herein are hereby incorporated by reference in their entirety as if each individual publication or patent was specifically and individually indicated to be incorporated by reference.

We claim:

1. A method for producing a population of double-stranded oligonucleotides having improved fidelity on a solid support, the method comprising:
   (a) contacting, on a solid support, a plurality of support-bound single-stranded oligonucleotides with a solution comprising a primer and a polymerase enzyme under conditions suitable for a template-dependent synthesis reaction, thereby producing a plurality of double-stranded oligonucleotides comprising synthesized complementary oligonucleotides base paired with the support-bound single-stranded oligonucleotides, wherein the support-bound single-stranded oligonucleotides are bound on the solid support at their 3' ends and comprise error-free oligonucleotides and error-containing oligonucleotides;
   (b) denaturing the plurality of double-stranded oligonucleotides such that the synthesized complementary oligonucleotides are released in one or more droplets;
   (c) reannealing the synthesized complementary oligonucleotides in the one or more droplets to the support-bound single-stranded oligonucleotides, thereby producing reannealed double-stranded oligonucleotides comprising homoduplexes and heteroduplexes, wherein each of the heteroduplexes comprises a mismatch;
   (d) exposing the reannealed double-stranded oligonucleotides to a mismatch recognizing and cleaving component under conditions suitable for cleavage of the heteroduplexes, thereby cleaving at least a portion of the heteroduplexes; and
   (e) removing at least a portion of the cleaved heteroduplexes, thereby producing the population of double-stranded oligonucleotides having improved fidelity on the solid support.

2. A method for producing a population of double-stranded oligonucleotides having improved fidelity on a solid support, the method comprising:
   (a) synthesizing a first plurality of oligonucleotides in a chain extension reaction using a second plurality of support-bound oligonucleotides as templates in the presence of a solution comprising a primer, wherein the second plurality of oligonucleotides is bound on a solid support at their 3' ends and comprise an error-containing oligonucleotide having a sequence error at an error-containing position, thereby producing a first plurality of duplexes, wherein the first plurality of duplexes comprises homoduplexes;
   (b) denaturing the first plurality of duplexes, thereby releasing the first plurality of oligonucleotides in one or more droplets, wherein the first plurality of oligonucleotides comprise error-free oligonucleotides that are free of error at a position corresponding to the error-containing position of the error-containing oligonucleotide in the second plurality of oligonucleotides;
   (c) contacting the first plurality of oligonucleotides in the one or more droplets with the second plurality of oligonucleotides under hybridization conditions such that a second plurality of duplexes is formed, wherein the second plurality of duplexes comprise a mismatch-containing heteroduplex formed between the error-containing oligonucleotide and one of the error-free oligonucleotides;
   (d) cleaving the mismatch-containing heteroduplex by a mismatch recognizing and cleaving component; and
   (e) removing the mismatch-containing heteroduplex, thereby producing the population of double-stranded oligonucleotides having improved fidelity on the solid support.

3. The method of claim 1 or 2 further comprising selectively denaturing the population of double-stranded oligonucleotides having improved fidelity.

4. A method of assembling nucleic acid polymers comprising the steps of:
   (a) producing two or more populations of double-stranded oligonucleotides having improved fidelity according to the method of claim 1 or 2;
   (b) denaturing selected populations of the double-stranded oligonucleotides from the two or more populations of double-stranded oligonucleotides having improved fidelity, thereby releasing at least a first desirable pool and a second desirable pool of single-stranded oligonucleotides having improved fidelity in a solution;
   (c) combining the at least a first desirable pool and a second desirable pool of single-stranded oligonucleotides into a droplet;
   (d) subjecting the single-stranded oligonucleotides in the droplet to conditions suitable for hybridization, and
   (e) assembling the nucleic acid polymers by ligation, or by chain extension, or by chain extension and ligation of the single-stranded oligonucleotides.

5. The method of claim 2 wherein the second plurality of oligonucleotides are chemically synthesized on the solid support and immobilized within one or more features on the solid support.

6. The method of claim 2 wherein the first plurality of oligonucleotides are enzymatically synthesized on the solid support.

7. The method of claim 2 wherein the second plurality of oligonucleotides are attached to two or more features on the solid support and wherein after step (b), one or more of the first plurality of oligonucleotides diffuse away from the two or more features.

8. The method of claim 1 or 2 wherein the mismatch recognizing and cleaving component comprises a mismatch endonuclease.

9. The method of claim 1 or 2 wherein the mismatch recognizing and cleaving component performs a chemical cleavage.

10. The method of claim 1 or 2 wherein the removing step comprises buffer exchange.

11. The method of claim 1 or 2 wherein the solid support is a microarray.

12. The method of claim 1 wherein the removing step reduces the number of error-containing oligonucleotides on the solid support.

13. The method of claim 1 further comprising denaturing the population of double-stranded oligonucleotides having improved fidelity obtained in the removing step.

14. A method for producing at least one support-bound error-free oligonucleotide having a predefined sequence on a solid support, the method comprising:
   (a) synthesizing a first plurality of oligonucleotides on a solid support using a second plurality of support-bound oligonucleotides as templates in the presence of at least one primer, wherein the second plurality of support-bound oligonucleotides is bound on the solid support at their 3' ends,
      wherein the at least one primer is complementary to a primer binding site on the second plurality of oligonucleotides,
      wherein each of the second plurality of oligonucleotides has a predefined sequence, and wherein at least one of the second plurality of support-bound oligonucleotides comprises a sequence error;
   (b) releasing the first plurality of oligonucleotides in one or more droplets;
   (c) contacting the second plurality of support-bound oligonucleotides with the first plurality of oligonucleotides in the one or more droplets under hybridization conditions such that a plurality of double-stranded oligonucleotides is formed, wherein the plurality of double-stranded oligonucleotides comprises a double-stranded oligonucleotide having a mismatch with the sequence error;
   (d) contacting and cleaving the second plurality of double-stranded oligonucleotides with a mismatch binding agent, wherein the mismatch binding agent selectively binds and cleaves the double-stranded oligonucleotide having the mismatch; and
   (e) removing the double-stranded oligonucleotide having the mismatch, thereby producing the at least one support-bound error-free oligonucleotide having the predefined sequence on the solid support.

15. The method of claim 14 wherein the mismatch binding agent is a mismatch specific endonuclease.

16. The method of claim 15 wherein the mismatch specific endonuclease cleaves the nucleotide at the region of the mismatch.

17. The method of claim 15 wherein the mismatch specific endonuclease is a CEL enzyme.

18. The method of claim 14 wherein the first plurality of oligonucleotides in the releasing step is released under denaturing conditions.

19. The method of claim 14 wherein the second plurality of oligonucleotides is bound to one or more discrete features of the solid support and wherein the one or more features are selectively hydrated such that the second plurality of oligonucleotides are present within the one or more droplets.

20. The method of claim 19 wherein the synthesizing step further comprises selectively hydrating the one or more features by spotting a solution comprising the at least one primer, a polymerase, dNTPs, and a buffer capable of promoting primer extension.

21. The method of claim 14 further comprising releasing at least one error-free single-stranded oligonucleotide in solution.

* * * * *